United States Patent
Miles et al.

(10) Patent No.: US 9,908,933 B2
(45) Date of Patent: Mar. 6, 2018

(54) ANTIBODY THERAPY FOR AMYLOID BETA DISEASE

(71) Applicant: St. Vincent's Institute of Medical Research, Fitzroy, Victoria (AU)

(72) Inventors: Luke Anthony Miles, Fitzroy (AU); Michael William Parker, Fitzroy (AU); Tracy Leah Nero, Fitzroy (AU)

(73) Assignee: St. Vincent's Institute of Medical Research, Fitzroy, Victoria (AU)

( * ) Notice: Subject to any disclaimer, the term of this patent is extended or adjusted under 35 U.S.C. 154(b) by 0 days.

(21) Appl. No.: 14/910,172

(22) PCT Filed: Aug. 5, 2014

(86) PCT No.: PCT/AU2014/050172
§ 371 (c)(1),
(2) Date: Feb. 4, 2016

(87) PCT Pub. No.: WO2015/017900
PCT Pub. Date: Feb. 12, 2015

(65) Prior Publication Data
US 2016/0194385 A1 Jul. 7, 2016

(30) Foreign Application Priority Data
Aug. 5, 2013 (AU) .............................. 2013902922

(51) Int. Cl.
*C07K 16/18* (2006.01)
*A61K 39/395* (2006.01)
*G01N 33/53* (2006.01)
*C07H 21/04* (2006.01)
*G01N 33/68* (2006.01)

(52) U.S. Cl.
CPC ........... *C07K 16/18* (2013.01); *G01N 33/689* (2013.01); *G01N 33/6896* (2013.01); *C07K 2299/00* (2013.01); *C07K 2317/24* (2013.01); *C07K 2317/33* (2013.01); *C07K 2317/34* (2013.01); *C07K 2317/55* (2013.01); *C07K 2317/565* (2013.01); *C07K 2317/76* (2013.01); *G01N 2333/4709* (2013.01); *G01N 2800/2821* (2013.01); *G01N 2800/368* (2013.01)

(58) Field of Classification Search
CPC ............... C07K 16/18; C07K 2317/24; C07K 2317/33; C07K 2317/34; C07K 2317/55; C07K 2317/565; C07K 2317/76
See application file for complete search history.

(56) References Cited

FOREIGN PATENT DOCUMENTS

| EP | 1717250 A1 | 11/2006 |
|---|---|---|
| WO | 2004032868 A2 | 4/2004 |
| WO | 2008/060364 A2 | 5/2008 |
| WO | 2011161970 A1 | 12/2011 |
| WO | 2012104824 A1 | 8/2012 |

OTHER PUBLICATIONS

Mamo JCL et al. Plasma lipoprotein beta-amyloid in subjects with Alzheimer's disease or mild cognitive impairment. Ann. Clin. Biochem. 2008, 45:395-403.*
Adolfsson et al., "An Effector-Reduced Anti-β-Amyloid (Aβ) Antibody with Unique Aβ Binding Properties Promotes Neuroprotection and Glial Engulfment of Aβ", The Journal of Neuroscience, 32(28):9677-9689 (2012).
Filson, "12th international conference on Alzheimer's Disease. Part 2". I Drugs: The Investigational Drugs Journal. Current Drugs Ltd. GB. vol. 12. No. 9. Sep. 1, 2009. pp. 537-538.
Supplementary European Search report issued in corresponding European application No. EP14834839, dated Mar. 7, 2017.
International Search Report for corresponding application No. PCT/AU2014/050172 dated Nov. 27, 2014.

* cited by examiner

*Primary Examiner* — Kimberly A. Ballard
(74) *Attorney, Agent, or Firm* — McDonnell Boehnen Hulbert & Berghoff LLP

(57) ABSTRACT

The present disclosure relates generally to a protocol to treat or prevent diseases or conditions associated with pathological forms of amyloid beta (Aβ), including Alzheimer's disease. Enabled herein is a reagent for use in the treatment and prophylaxis of Aβ-associated pathological conditions.

16 Claims, 3 Drawing Sheets

ANTIBODY THERAPY FOR AMYLOID BETA DISEASE

FILING DATA

This application is associated with and claims priority from Australian Provisional Patent Application No. 2013902922, filed on 5 Aug. 2013, entitled "An antibody therapy for amyloid beta disease", the entire contents of which, are incorporated herein by reference.

BACKGROUND

Field

The present disclosure relates generally to a protocol to treat or prevent diseases or conditions associated with pathological forms of amyloid beta (Aβ), including Alzheimer's disease. Enabled herein is a reagent for use in the treatment and prophylaxis and diagnosis of Aβ-associated pathological conditions.

Prior Art

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Alzheimer's disease is a degenerative brain disorder characterized histologically by neuritic plaques found primarily in association with the cortex, limbic system and basal ganglia. These neuritic plaques comprise a cleavage product of amyloid precursor protein (APP), a type I transmembrane glycoprotein.

The cleavage product of APP is β-amyloid peptide or Aβ. Incorrect processing of APP can result in pathological forms of Aβ (Tanzi et al. (1996) *Neurobiol Dis* 3:159-168; Hardy (1996) *Ann Med* 28:255-258; Schenk et al. (1999) *Nature* 400:173-177). These pathological forms include $Aβ_{1-42}$ and $Aβ_{1-43}$ which have been detected as predominant species in the neurite plaques.

Bard et al. (2000) *Nature Medicine* 6:916-919 showed that peripheral administration of antibodies directed against Aβ can reduce plaque burden. Bard et al. (2003) *Proc. Natl. Acad. Sci. USA* 100:2023-2028 subsequently showed that Fc-mediated phagocytosis by microglial cells or macrophages is associated with plaque clearance. Hence, antibody therapy has the potential to treat Alzheimer's disease.

This is supported by non-Fc-mediated mechanisms being found to be associated with Aβ clearance in immunotherapy (Bacskai et al. (2002) *J. Neurosci.* 22:7873-7878; Das et al. (2003) *J. Neurosci.* 23:8532-9538).

One attempt at immunotherapy was the humanized antibody, Bapineuzumab or Bapi, developed by Pfizer and Johnson & Johnson. Bapi targets neurotoxic Aβ (Salloway et al. (2009) *Neurology* 73:2061-2070) at the extreme N-terminus in a helical conformation (Miles et al. (2013) *Sci Rep* 3:1-8) [doi:10.1038/srep01302]. Such Aβ forms with the N-terminal truncations comprise approximately 60% of Aβ deposits in the Alzheimer's diseased brains. Bapi was, however, shown to be toxic at higher doses.

Another antibody is Solanezumab (Eli Lilly). This antibody targets monomeric Aβ in the mid-region of the peptide and was partially efficacious in mild cases of Alzheimer's disease (Hardy (2014) *N Engl J Med* 370(4):377-378).

However, it appears that Solanezumab may be ineffective at reversing the symptoms in the later stages of Alzheimer's disease (Panza et al. (2014) *Expert Opin Biol Ther*:1-12 PMID 24981190).

Crenezumab (Genentech Inc.) also targets the mid-region of AB. It appears to stimulate microglia to a level sufficient to clear Aβ but without inducing an inflammatory response (Adolfsson et al. (2012) *J. Neuroscience* 32(28):9677-9689).

Ponezumab (Pfizer) targets the C-terminal end of $Aβ_{1-40}$ but is unable to bind to elongated forms such as $Aβ_{1-42}$ and $Aβ_{1-43}$. Ponezumab was not efficacious in reducing biomarkers of Alzheimer's disease or cognitive decline (Liu et al. (2014) *Mol Neurobiol*:PMID 24733588). Another monoclonal antibody which has the same binding specificity as Ponezumab is referred to as Mab 2286 (Rosenthal et al. USSN 2011/038861, 2004/0146512 and 2007/0160616). Mab 2286 also does not bind to $Aβ_{1-42}$ and $Aβ_{1-43}$.

There is a need to further develop an immunotherapeutic approach to the treatment of disease conditions associated with toxic Aβ forms and their diagnosis.

SUMMARY

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present disclosure teaches the generation of an antibody and derivatives thereof which target $Aβ_{1-40}$ and its C-terminally extended forms including $Aβ_{1-42}$ and $Aβ_{1-43}$. The inventors analyzed the molecular basis of antibody engagement with Aβ. The 3D structure of a Fab binding fragment of the variable domain of Mab 2286 (referred to herein as "Fab 2286") was determined to near atomic resolution. Fab 2286 is a chimera comprising the mouse variable region of Mab 2286 transplanted onto a human scaffold. Fab 2286 comprises $V_H$ and $V_L$ from Mab 2286 and $C_H$ and $C_L$ from a human template. This antibody exhibits similar specificity as Ponezumab to the C-terminus of $Aβ_{1-40}$ and does not react with $Aβ_{1-42}$ or $Aβ_{1-43}$ or other elongated forms such as $Aβ_{3-42}$, $Aβ_{4-42}$, $Aβ_{pyroGlu3-42}$ and $Aβ_{pyroGlu11-42}$. The analysis of chimeric Fab 2286 revealed a hydrophobic cavity in the Fab 2286 surface suitable for binding amyloid beta peptide. The amino acid sequences of Ponezumab and Fab 2286 show little similarity in the complementarity determining regions, but comparison of the 3D structures (Protein Data Bank entries 3U0T and 3U0W, respectively) revealed some potential spacial similarities for ligand engagement. Structural analysis of the Ponezumab-Aβ complex revealed a buried Aβ terminal carboxyl location that excluded cross reactivity with C-terminally elongated Aβ species. A modification is prepared of the proposed $Aβ_{1-40}$ C-terminus binding site of Fab 2286 at the glutamic acid (E; Glu) at residue 50 in the heavy variable chain of Fab 2286 [Glu50]. The substitution to another amino acid (Glu50Xaa), wherein Xaa is not glutamic acid, substantially improves affinity for the $Aβ_{1-40}$ ligand and enables binding to the C-terminally elongated Aβ species. In an embodiment, Xaa is selected from the list consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, pyrrolysine and selenocysteine. In an embodiment, Xaa is a basic amino acid such as arginine, lysine or histidine. In an embodiment, Xaa is alanine. In a particular embodiment, Xaa is arginine.

Accordingly, enabled herein is an antibody that specifically binds to the C-terminal end portion of $A\beta_{1\text{-}40}$ and to C-terminally extended toxic forms thereof. In an embodiment, the antibody is a derivative of Fab 2286 and is referred to herein as a "Fab 2286-like antibody". Fab 2286 comprises the antigen binding fragment of Mab 2286 grafted onto a human scaffold constant region. In an embodiment, the instant disclosure teaches a Fab 2286-like antibody comprising an amino acid substitution at glutamic acid (E) in its heavy chain in the amino acid sequence WIGE to generate the sequence WIGX. In an embodiment, the substitution is to an amino acid selected from the list consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, pyrrolysine and selenocysteine. In an embodiment, the substitution is to a basic amino acid such as arginine, lysine or histidine. In an embodiment, the substitution is to an alanine. In an embodiment, the substitution is to an arginine. The Fab 2286-like antibody may have one or more other mutations. The Fab 2286-like antibody may be conjugated to any light and heavy chain constant region and be subject to mammalianization such as humanization (or deimmunization). In terms of testing the antibody in an animal model, the antibody may, for example, be subject to murinization.

Further enabled herein is a method for treating a disease or condition characterized by the presence of aberrant or toxic forms of Aβ including C-terminally elongated forms (e.g. $A\beta_{1\text{-}42}$, $A\beta_{1\text{-}43}$, $A\beta_{3\text{-}42}$, $A\beta_{4\text{-}42}$, $A\beta_{pyroGlu3\text{-}42}$ and $A\beta_{pyroGlu11\text{-}42}$) as well as covalently cross-linked pathogenic forms of Aβ multimers. The method comprises the administration of a Fab 2286-like antibody comprising a mutation in its heavy chain variable region which enables it to bind to C-terminally elongated pathogenic forms of Aβ. The mutation is a Glu50Xaa substitution in SEQ ID NO: 1. An example is a Glu50Arg substitution as depicted in SEQ ID NO:2. Other modified forms of the heavy chain which includes the Glu50Arg substitution are provided in SEQ ID NOs:6 and 8. As indicated above, however, the glutamic acid is changed to an amino acid selected from the list consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, pyrrolysine and selenocysteine. In an embodiment, the amino acid is a basic amino acid such as arginine, lysine or histidine. In an embodiment, the amino acid is alanine. In an embodiment, the amino acid is arginine.

Diseases and conditions contemplated herein include Alzheimer's disease, Down's syndrome, cognitive impairment or memory loss, Parkinson's disease multi-infarct dementia, cerebral amyloid angiopathy, glaucoma and a vascular disorder caused by pathogenic Aβ peptide in blood vessels (e.g. stroke and hereditary cerebral hemorrhage with amyloidosis-Dutch type [HCHWA-D]). The subject antibody may also be used to capture and/or detect toxic forms of Aβ associated with the above-listed conditions. In terms of diagnosis, another condition contemplated herein is pre-eclampsia. Whilst pre-eclampsia and a neurological condition such as Alzheimer's disease share no clinical features in common, the pre-eclampsia susceptibility gene, STOX-1, is abundantly expressed in the brain and transactivates LRRTM3 in neural cells which promotes elevated Aβ processing. Hence, the presence of toxic forms of Aβ in urine is potentially indicative of pre-eclampsia. The Fab 2286-like antibody may act to promote microglial-mediated removal of pathogenic Aβ species in the brain and/or through the "peripheral sink" route to induce an equilibrium shift to remove Aβ from the brain to the blood stream where it is removed by various immune mechanisms.

The treatment may also include ameliorating symptoms or delaying onset of symptoms of an Aβ pathology such as Alzheimer's disease.

Another aspect contemplated herein is a method of detecting a toxic form of Aβ in a sample from a subject, the method comprising identifying binding between the Aβ form and Fab 2286-like antibody. The antibody may also be used to capture an Aβ form which is then detected by, for example, another antibody specific for an epitope on Aβ or by an anti-immunoglobulin antibody which binds to the Fab 2286-like antibody.

Diagnostic applications extend to Alzheimer's disease, Down's syndrome, cognitive impairment or memory loss, Parkinson's disease multi-infarct dementia, cerebral amyloid angiopathy, glaucoma and a vascular disorder caused by pathogenic Aβ peptide in blood vessels (e.g. stroke and hereditary cerebral hemorrhage with amyloidosis-Dutch type [HCHWA-D]) and pre-eclampsia. Whilst a blood-based test is proposed for most conditions, for pre-eclampsia, a urine-based test is proposed. Cerebral spinal fluid may also be tested. In an embodiment, taught herein is a dipstick comprising Fab 2286-like antibody immobilized thereon for use in detecting toxic forms of Aβ in a biological sample. In an embodiment, the sample is urine and the condition diagnosed is pre-eclampsia.

TABLE 1

Summary of sequence identifiers

| SEQUENCE ID NO: | DESCRIPTION |
|---|---|
| 1 | Amino acid sequence of heavy chain variable region of Fab 2286 antibody |
| 2 | Amino acid sequence of heavy chain of Fab 2286-like antibody comprising Glu50Arg substitution |
| 3 | Amino acid sequence of light chain (hkappa) of Fab 2286 (and Fab 2286-like antibody) |
| 4 | Amino acid sequence of $A\beta_{1\text{-}28}$ |
| 5 | Amino acid sequence of $A\beta_{1\text{-}40}$ |
| 6 | Amino acid sequence of $A\beta_{1\text{-}42}$ |
| 7 | Amino acid sequence of $A\beta_{1\text{-}43}$ |
| 8 | Amino acid sequence of $A\beta_{35\text{-}40}$ |

TABLE 1-continued

Summary of sequence identifiers

| SEQUENCE ID NO: | DESCRIPTION |
|---|---|
| 9 | Amino acid sequence of murinized Fab 2286-like antibody heavy chain conjugated to human gamma-1 immunoglobulin (hG1) heavy constant region with Glu50Arg substitution |
| 10 | Amino acid sequence of chimeric Fab 2286 antibody heavy chain variable region |
| 11 | Amino acid sequence of chimeric Fab 2286-like antibody heavy chain variable region |
| 12 | Nucleotide sequence of Mab 2286 heavy chain (variable domain and constant domain 1 [CH1]) |
| 13 | Amino acid sequence of Mab 2286 heavy chain (variable domain and constant domain 1 [CH1]) |
| 14 | Nucleotide sequence of Mab 2286 light chain |
| 15 | Amino acid sequence of Mab 2286 light chain |
| 16 | Nucleotide sequence of synthetic DNA construct encoding Fc portion of murine gamma heavy chain ((GenBank: AAA75163.1) of Mab 2286 |
| 17 | Amino acid sequence of Fc portion of murine gamma heavy chain (GenBank: AAA75163.1) of Mab 2286 |
| 18 | Nucleotide sequence of murine heavy B encoding Glu to Arg substitution |
| 19 | Amino acid sequence of murine heavy B with Glu to Arg substitution |
| 20 | Nucleotide sequence of murine light chain of Fab 2286-like antibody |
| 21 | Amino acid sequence of murine light chain of Fab 2286-like antibody |

Amino acid abbreviations used herein are defined in Table 2.

TABLE 2

Amino acid three and single letter abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Pyrrolysine | Pyl | O |
| Selenocysteine | Sec | U |
| Any residue | Xaa | X |

BRIEF DESCRIPTION OF THE FIGURES

Some figures contain color representations or entities. Color photographs are available from the Patentee upon request or from an appropriate Patent Office. A fee may be imposed if obtained from a Patent Office.

DETAILED DESCRIPTION

Figure 1:
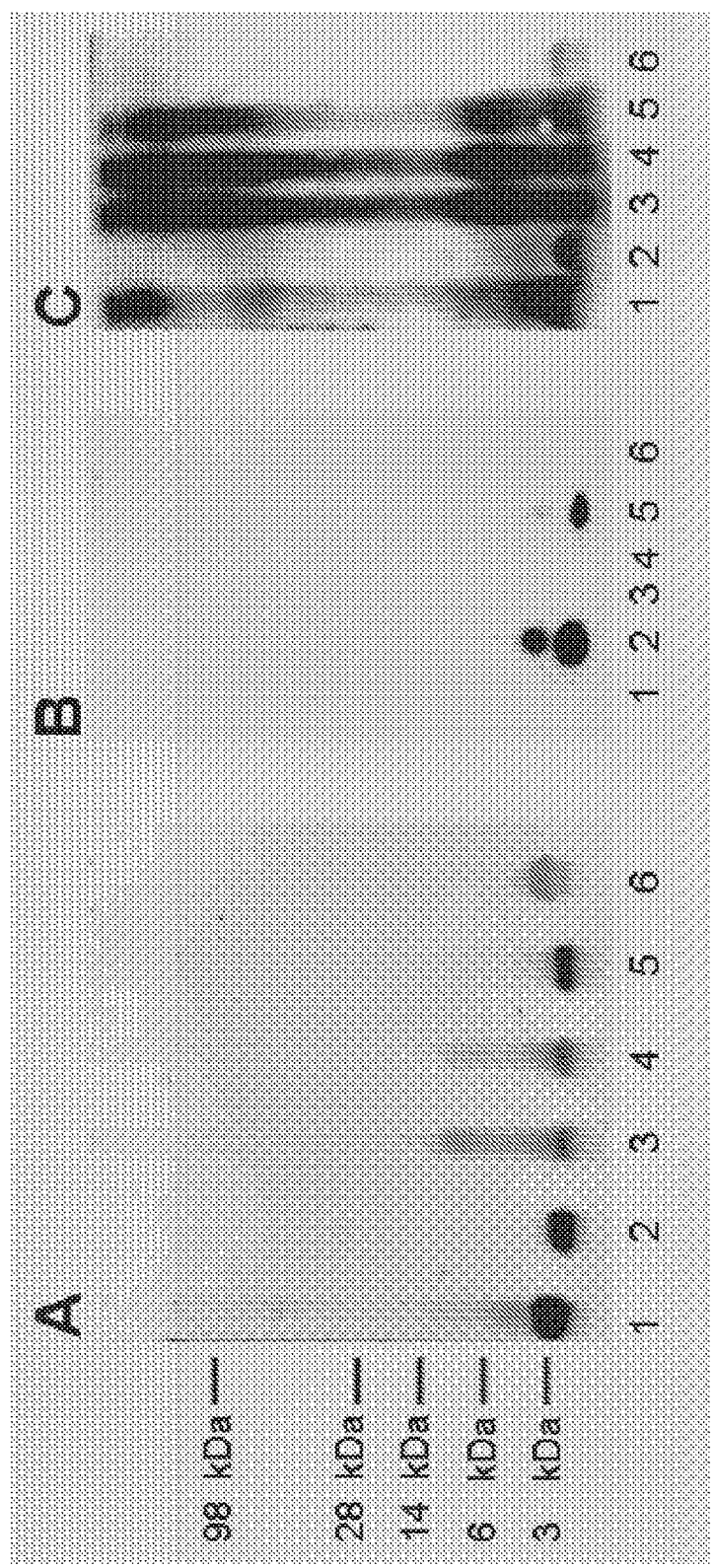
FIG. 1A through C are photographical representations of SDS-PAGE analysis of synthetic Aβ preparations. Detected by (A) Coomassie stain, (B) anti-Aβ40 C-terminus specific Mab 2286 Western Blot and (C) anti-Aβ$_{2-7}$ specific Mab WO2 Western Blot. In each panel, lanes represent: (1) Aβ$_{1-40}$ aged for 21 days at room temperature in PBS; (2) freshly prepared, from 2,2,2-trifluoroethanol (TFE)-treated and lyophilized stock, Aβ$_{1-40}$; (3) Aβ$_{1-42}$ aged for 21 days at room temperature in phosphile buffered saline (PBS); (4) freshly prepared, from TFE-treated and lyophilized stock, Aβ$_{1-42}$; (5) 1:1 mixture of Aβ$_{1-40}$ and Aβ$_{1-42}$ aged overnight at room temperature in PBS; (6) Aβ$_{1-28}$ freshly prepared, from TFE-treated and lyophilized stock.

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a mutation" includes a single mutation, as well as two or more mutations; reference to "an antibody" includes a single antibody, as well as two or more antibodies; reference to "the disclosure" includes a single reference to "the disclosure" and includes single and multiple aspects taught by the disclosure; and so forth. Aspects taught and enabled herein are encompassed by the term "invention". All such aspects are enabled within the width of the present invention.

Disclosed herein is an antibody which binds to Aβ$_{1-40}$ ("Aβ$_{40}$") as well as C-terminally elongated pathogenic forms of Aβ, including Aβ$_{1-42}$ ("Aβ$_{42}$") and Aβ$_{1-43}$ ("Aβ$_{43}$") as well as covalently linked multimers thereof. A "multimer" includes an oligomer. The antibody comprises a mature heavy chain having the amino acid sequence as set forth in SEQ ID NO: 1 with the proviso that in the sequence WIGE, the glutamic acid (E) is substituted for another amino acid residue, i.e. Glu50Xaa. In an embodiment, Xaa is selected from the list consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, pyrrolysine and selenocysteine. In an embodiment, Xaa is a basic amino acid such as arginine, lysine or histidine. In an embodiment, Xaa is alanine. In an embodiment, Xaa is arginine such as depicted in SEQ ID NO:2. Other forms are provided in SEQ ID NOs:9 and 11. The amino acid sequence of its light chain is set forth in SEQ ID NO:3. The mature heavy chain is derived from an antigen-binding fragment of Mab 2286 (a Fab 2286 fragment) and the antibody of the present disclosure is referred to as an "Fab 2286-like antibody". It is also referred to as "Aβ Fab mutant". The Mab 2286 precursor antigen binding fragment is referred to as "Fab 2286" or "Aβ Fab wt". The Fab 2286-like antibody differs from Ponezumab and Mab 2286 by its ability to bind to C-terminally elongated Aβ species. These include $A\beta_{1-42}$ and $A\beta_{1-43}$ as well as $A\beta_{3-42}$, $A\beta_{4-42}$, $A\beta_{pyroGlu3-42}$ and $A\beta_{pyroGlu11-42}$. The Fab 2286-like antibody may also comprise one or more additional amino acid substitutions, additions and/or deletions. In addition, the Fab 2286-like antibody may be conjugated to any heavy and light constant regions. For example, in an embodiment, the Fab 2286-like antibody is conjugated to human kappa-1 immunoglobulin (hkappa) light chain and human gamma-1 immunoglobulin (hG1) heavy chain constant regions. In one example, the heavy chain variable and constant regions ($V_H+C_H$) have an amino acid sequence set forth in SEQ ID NO:9. Furthermore, the antibody may be mammalianized so that it can be administered to a particular mammal such as a mouse, rat, pig, sheep or monkey. In an embodiment, the mammal is a human and the antibody is humanized or deimmunized. In terms of testing the antibody in an animal model such as a mouse model, it may also be subject to murinization.

Accordingly, enabled herein is an isolated Fab 2286-like antibody which binds to $A\beta_{1-40}$ and a C-terminally elongated form thereof, the antibody comprising a modified Fab 2286 wherein a mature heavy chain variable region comprises an amino acid sequence as set forth in SEQ ID NO:1 with the proviso that the amino acid residue at position 50 is not glutamic acid, wherein the numbering of the amino acid sequence WIGE in Fab 2286 (SEQ ID NO:1) represents residues 47 to 50 or comprising one or more other amino acid substitutions, additions and/or deletions to the amino acid sequence of SEQ ID NO:1.

Enabled herein is an isolated antibody comprising a mature heavy chain as set forth in SEQ ID NO:2 or one or more amino acid substitutions, additions and/or deletions to the amino acid sequence set forth in SEQ ID NO:2 provided that the amino acid residue at position 50 is arginine (R) [50 Arg]. In an embodiment, the amino acid sequence comprises at least 90% similarity to SEQ ID NO:2 provided it still contains the Glu50Arg substitution.

Enabled herein is an isolated antibody comprising a mature heavy chain as set forth in SEQ ID NO:9 or one or more amino acid substitutions, additions and/or deletions to the amino acid sequence set forth in SEQ ID NO:9 provided that the amino acid residue at position 50 is arginine (R) [50 Arg]. In an embodiment, the amino acid sequence comprises at least 90% similarity to SEQ ID NO:9 provided it still contains the Glu50Arg substitution.

Enabled herein is an isolated antibody comprising a mature heavy chain as set forth in SEQ ID NO:1 or one or more amino acid substitutions, additions and/or deletions to the amino acid sequence set forth in SEQ ID NO:11 provided that the amino acid residue at position 50 is arginine (R) [50 Arg]. In an embodiment, the amino acid sequence comprises at least 90% similarity to SEQ ID NO:1 provided it contains the Glu50Arg substitution.

To take into account variations in the heavy chain, in the amino acid sequence WIGE of SEQ ID NO:1 (mature heavy chain variable region of Fab 2286), the E is at position 50 and in the Fab 2286-like antibody, the sequence is WIGR (see SEQ ID NO:2, 9 and 11). This is also referred to herein as a Glu50Arg substitution of the mature heavy chain variable region of Fab 2286. However, the present invention extends to a substitution of E at position 50 to any amino acid residue such as alanine, arginine, asparagine, aspartic acid, cysteine, glutamine, glycine, histidine, isoleucine, leucine, lysine, methionine, phenylalanine, proline, serine, threonine, tryptophan, tyrosine, valine, pyrrolysine or selenocysteine. In an embodiment, the substitution is to a basic amino acid residue such as arginine, lysine or histidine. In an embodiment, the substitution is to an alanine. In an embodiment, the substitution is to an arginine. In an embodiment, the present invention extends to a Fab 2286-like antibody comprising a heavy chain variable region as set forth in SEQ ID NO: 1 with the exception that in the sequence WIGE at amino acids 47 to 50, the sequence is selected from WIGA, WIGR, WIGN, WIGD, WIGC, WIGQ, WJGG, WIGH, WIGI, WIGL, WIGK, WIGM, WIGF, WIGP, WIGS, WIGT, WIGW, WIGY, WIGV, WIGO and WIGU. In an embodiment, the sequence is WIGR, WIGK, WIGH, WIGA or WIGM. In an embodiment, the sequence is WIGR. Reference to "at least 90%" amino acid sequence similarity means 90, 91, 92, 93, 94, 95, 96, 97, 98, 99 or 100% similarity. By "similarity" includes "identity".

In a related embodiment, enabled herein is an isolated antibody which binds to $A\beta_{1-40}$ or C-terminally elongated forms thereof or covalently linked multimers thereof, the antibody comprising a modified form of Fab 2286 wherein a mature heavy chain variable region comprises a modified amino acid sequence set forth in SEQ ID NO:1 with the proviso that the amino acid residue at position 50 is not glutamic acid (E), wherein the numbering of the amino acid sequence WIGE in Fab 2286 (SEQ ID NO:1) represents amino acid residues 47 to 50 or comprising one or more amino acid substitutions, additions and/or deletions to the amino acid sequence of SEQ ID NO: 1.

In an embodiment, the amino acid residue at position 50 is selected from the list consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, pyrrolysine and selenocysteine. In an embodiment, the amino acid residue at position 50 is a basic amino acid such as arginine, lysine or histidine. In an embodiment, the amino acid residue at position 50 is alanine. In an embodiment, the amino acid residue at position 50 is arginine.

The present disclosure is instructional on a Fab 2286-like antibody comprising a mature heavy chain variable region comprising the amino acid sequence set forth in SEQ ID NO:2 wherein the Fab 2286-like antibody binds to $A\beta_{1-40}$ and to C-terminally elongated forms thereof.

Other examples of the heavy chain variable regions are found in SEQ ID NOs:9 and 11.

Reference to "C-terminally elongated forms" of $A\beta_{1-40}$ includes $A\beta_{1-42}$, $A\beta_{1-43}$, $A\beta_{3-42}$, $A\beta_{4-42}$, $A\beta_{pyroGlu3-42}$ and $A\beta_{pyroGlu11-42}$.

Enabled herein is an isolated polynucleotide encoding an amino acid sequence of a mature heavy chain variable region of an antibody which binds to $A\beta_{1-40}$ and C-terminally elongated forms thereof or covalently linked multimers thereof, the antibody comprising a modified form of Fab 2286 wherein a mature heavy chain variable region comprises the amino acid sequence set forth in SEQ ID NO: 1 wherein the amino acid at position 50 is not glutamic acid or comprising one or more other amino acid substitutions, additions and/or deletions to the amino acid sequence of SEQ ID NO: 1. The numbering of the amino acid sequence WIGE in Fab 2286 (SEQ ID NO:1) represents amino acid residues 47 to 50. In an embodiment, the amino acid at position 50 is selected from the list constituting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, pyrrolysine and selenocysteine. In an embodiment, the amino acid at position 50 is a basic amino acid such as arginine, lysine or histidine. In an embodiment, the amino acid at position 50 is alanine. In an embodiment, the amino acid residue at position 50 is arginine. Hence, in an embodiment, the polynucleotide encodes SEQ ID NO:2. Cells and vectors comprising the polynucleotide are also enabled herein. Polynucleotide encoding SEQ ID NOs:9 and 11 are also contemplated herein as well as polynucleotide sequence which have at least 90% identity to the nucleotide sequence encoding each of SEQ ID NO:2, 9 or 11 or a nucleic acid capable of hybridizing under medium or high stringency conditions to the nucleotide sequence encoding SEQ ID NO:2, 9 or 11 provided the nucleotide sequence encodes Glu50Arg substitution. In an embodiment, the nucleotide sequence is SEQ ID NO:18 or a nucleotide having at least 90% identity to SEQ ID NO:18 or a nucleotide sequence which hybridizes to the complement of SEQ ID NO: 18 under medium or high stringency conditions. In relation to a nucleotide sequence, "at least 90%" means 90, 91, 92, 93, 94, 95, 96, 97, 98, 99 or 100%.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In an embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (e.g. GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997) *Nucl. Acids. Res.* 25:3389. A detailed discussion of sequence analysis can be found in Unit 19.3 of Ausubel et al. (*In: Current Protocols in Molecular Biology*, John Wiley & Sons Inc. 1994-1998).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Reference to medium stringency includes and encompasses from at least about 16% v/v to at least about 30%0/v/v formamide and from at least about 0.5 M to at least about 0.9 M salt for hybridization, and at least about 0.5 M to at least about 0.9 M salt for washing condition. Reference to high stringency includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty (1962) *J. Mol. Biol.* 5:109). However, the $T_m$ of a duplex DNA decreases by 1° C. with every increase of 1% in the number of mismatch base pairs (Bonner and Laskey (1974) *Eur. J. Biochem.* 46:83). Formamide is optional in these hybridization conditions. Accordingly, particularly preferred levels of stringency are defined as follows: low stringency is 6×SSC buffer, 0.1% w/v SDS at 25°-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The Fab 2286-like antibody disclosed herein is useful in the treatment of a subject with a disease or condition associated with or characterized by the presence of pathogenic or toxic forms of Aβ species. The C-terminally elongated Aβ species may also be in the form of cerebral deposits. Such diseases or conditions include Alzheimer's disease, Down's syndrome, cognitive impairment or memory loss, Parkinson's disease, multi-infarct dementia, cerebral amyloid angiopathy, glaucoma and a vascular disorder caused by pathogenic Aβ peptide in blood vessels (e.g. stroke and hereditary cerebral hemorrhage with amyloidosis-Dutch type [HCHWA-D]). Generally, the subject is a human although for testing purposes, non-human mammalian subjects may be tested. In an example, a humanized antibody is used in humans and a murinize form is used for mice or rats. In an embodiment, the subject is a companion animal such as a dog or cat (using caninized and felinized antibodies, respectively). See, for example, SEQ ID NOs:9 and 11.

Hence, the instant disclosure teaches a method for the treatment or prophylaxis of a condition associated with or characterized by the presence of a pathogenic form of Aβ comprising a C-terminally elongated species of Aβ, the method comprising administering to a subject in need of treatment an effective amount of an antibody comprising a mature heavy chain having a modified amino acid sequence set forth in SEQ ID NO: 1 with the proviso that the amino acid residue at position 50 is not glutamic acid, using a numbering system where the amino acid sequence WIGE in Fab 2286 (SEQ ID NO:1) is at positions 47 to 50 or an amino acid sequence with one or more other amino acid substitutions, additions and/or deletions thereto. In an embodiment, the amino acid at position 50 is selected from the list consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, pyrrolysine and selenocysteine. In an embodiment, the amino acid at position 50 is a basic amino acid such as arginine, lysine or histidine. In an embodiment, the amino acid at position 50 is alanine. In an embodiment, the amino acid at position 50 is arginine.

In an embodiment, the instant disclosure teaches a method for the treatment or prophylaxis of a condition associated with or characterized by the presence of a pathogenic form of Aβ comprising a C-terminally elongated species of Aβ, the method comprising administering to a subject in need of treatment an effective amount of an antibody comprising a mature heavy chain having the amino acid sequence set forth in SEQ ID NO:2 or an amino acid sequence with one or more amino acid substitutions, additions and/or deletions thereto with the proviso that the amino acid residue at position 50 is R, using a numbering system where the amino acid sequence WIGE in Fab 2286 (SEQ ID NO:1) is at positions 47 to 50.

The effective amount of antibody includes an amount sufficient for microglia to be stimulated to facilitate removal of pathogenic forms of Aβ to which the antibody binds. Generally, the antibody does not substantially provoke an inflammatory response, the Fab 2286-like antibody promotes clearance of pathogenic Aβ species. This can be via microglial removal of Aβ in the brain or via a shift in the equilibrium of Aβ from the brain to the circulatory blood system ("peripheral sink").

Enabled herein is a method of treating or ameliorating symptoms of a neurological condition selected from Alzheimer's disease, Down's syndrome, cognitive impairment or memory loss, Parkinson's disease, multi-infarct dementia, cerebral amyloid angiopathy, glaucoma, stroke and HCHWA-D or other adverse event involving amyloidosis in a subject, the method comprising administering to the subject, an effective amount of a Fab 2286-like antibody comprising a mature heavy chain variable region having a modified amino acid sequence set forth in SEQ ID NO: 1 with the proviso that the amino acid residue at position 50 is not glutamic acid (E) using a numbering system where the amino acid sequence WIGE of Fab 2286 (SEQ ID NO: 1) is at positions 47 to 50 or having one or more other amino acid substitutions, additions and/or deletions thereto. In an embodiment, the amino acid substitution may also be referred to as Glu50Xaa in the heavy chain variable region of Fab 2286. In an embodiment, Xaa is selected from the list consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, pyrrolysine and selenocysteine. In an embodiment, Xaa is a basic amino acid residue such as arginine, lysine or histidine. In an embodiment, Xaa is alanine. In a particular embodiment, Xaa is arginine (i.e. the substitution is Glu50Arg).

The term "Fab 2286-like antibody" means that the Fab 2286 antibody has undergone a modification to the mature heavy chain variable region to substitute the E in the amino acid sequence WIGE at positions 47 to 50 to an R (i.e. WIGR) [Glu50Arg] or another amino acid [Glu50Xaa], wherein Xaa is not glutamic acid. One or more other amino acid substitutions, additions and/or deletions may also be made to the mature heavy chain or a light chain. The Fab 2286-like antibody, however, binds to $A\beta_{1-40}$ and C-terminally elongated forms thereof such as $A\beta_{1-42}$ and $A\beta_{1-43}$. In addition, the Fab 2286-like antibody may be conjugated to any light and heavy chain constant region scaffold. The original 2286 antibody ($V_L+C_L$; $V_H+C_H$) is referred to as Mab 2286. In an embodiment, the Fab 2286-like antibody is conjugated to heavy and light chain constant regions of any antibody.

The antibody may also bind to covalently bound multimers of these Aβ species.

In an embodiment, the present disclosure teaches a method for the treatment or prophylaxis of Alzheimer's disease in a subject, the method comprising administering to the subject an effective amount of an Fab 2286-like antibody having a modification to its mature heavy chain to substitute an E in the amino acid sequence WIGE to X (WIGX), wherein X is any amino acid except glutamic acid. In an embodiment, X is R (WIGR).

One or more other amino acid substitutions, additions and/or deletions may also be made to the heavy or light chain. In one embodiment, the $V_L+C_L$ comprises an amino acid sequence as set forth in SEQ ID NO:9.

The inventors analyzed the molecular basis of antibody engagement of Aβ epitopes. The 3D Fab structure (Fab 2286) was determined to near atomic resolution of the variable domain of Mab 2286. Fab 2286 is a chimera comprising the mouse variable region of Mab 2286 transplanted onto a human scaffold. Fab 2286 is $V_H$ and $V_L$ from Mab 2286 and $C_H$ and $C_L$ from a human template. The analysis revealed a hydrophobic cavity in the Fab 2286 binding site in which the C-terminal region of $A\beta_{1-40}$ was modeled. Data further revealed a buried terminal carboxyl location that excluded cross reactivity with C-terminally elongated Aβ species. Modification of the glutamic acid (E) at residue 50 by the substitution to another amino acid residue in the mature heavy chain variable region enables binding to the C-terminally elongated Aβ species.

Reference to an "antibody" includes an immunoglobulin molecule which binds to a specific target. In the case of the Fab 2286-like antibody of the instant disclosure, the specific target is the C-terminal end of $A\beta_{1-40}$ or C-terminally elongated Aβ species such as $A\beta_{1-42}$ and $A\beta_{1-43}$ as well as $A\beta_{3-42}$, $A\beta_{4-42}$, $A\beta_{pyroGlu3-42}$ and $A\beta_{pyroGlu11-42}$. The immunoglobulin binds to the C-terminal end of the elongated pathogenic forms of Aβ. Further covered herein are fragments of antibodies such as Fab, Fab', F(ab')$_2$ and Fv fragments, single chain (ScFv) forms, mutants, fusion proteins comprising a portion of the Fab 2286-like antibody and synthetically modified derivatives. In an embodiment, the Fab 2286-like antibody is conjugated to hkappa-1 light chain and hG1 heavy chain constant regions.

As used herein, an "effective dosage" or "effective amount" of the Fab 2286-like antibody or a pharmaceutical composition comprising same is an amount sufficient to effect beneficial or desired results. For prophylactic use, beneficial or desired results include results such as eliminating or reducing the risk, lessening the severity, or delaying the outset of the disease, including biochemical, histological and/or behavioral symptoms of the disease, its complications and intermediate pathological phenotypes presenting during development of the disease. Such a disease is a disease or condition associated with pathogenic forms of Aβ. Examples include Alzheimer's disease, Down's syndrome, cognitive impairment or memory loss, Parkinson's disease, multi-infarct dementia, cerebral amyloid angiopathy, glaucoma and a vascular disorder caused by pathogenic Aβ peptide in blood vessels (e.g. stroke and hereditary cerebral hemorrhage with amyloidosis-Dutch type [HCHWA-D]). For therapeutic use, beneficial or desired results include clinical results such as inhibiting, suppressing or reducing the formation of amyloid plaques, reducing, removing, clearing amyloid plaques, improving cognition, reversing or slowing cognitive decline, sequestering or increasing soluble Aβ peptide circulating in biological fluids, decreasing one or more symptoms resulting from the disease (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, delaying the progression of the disease, and/or prolonging survival of patients. An effective dosage can be administered in one or more administrations. For purposes of the present disclosure, an effective dosage of antibody, or pharmaceutical composition is an amount sufficient to accomplish prophylactic or therapeutic treatment either directly or indirectly. As is understood in the clinical context, an effective dosage of the Fab 2286-like antibody or pharmaceutical composition comprising same may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this disclosure, beneficial or desired clinical results include, but are not limited to, one or more of the following: inhibiting, suppressing or reducing the formation of amyloid plaques, reducing, removing, or clearing amyloid plaques, improving cognition, reversing or slowing cognitive decline, sequestering soluble Aβ peptide circulating in biological fluids, reducing Aβ peptide (including soluble, oligomeric and deposited) in a tissue (such as brain), inhibiting, slowing and/or reducing accumulation of Aβ peptide in the brain, inhibiting, slowing and/or reducing toxic effects of Aβ peptide in a tissue (such as brain), decreasing symptoms resulting from the disease, increasing the quality of life of those suffering from the disease, decreasing the dose of other medications required to treat the disease, delaying the progression of the disease, and/or prolonging survival of patients. Reference to disease includes Alzheimer's disease, Down's syndrome, cognitive impairment or memory loss, Parkinson's disease, multi-infarct dementia, cerebral amyloid angiopathy, glaucoma and a vascular disorder caused by pathogenic Aβ peptide in blood vessels (e.g. stroke and hereditary cerebral hemorrhage with amyloidosis-Dutch type [HCHWA-D]).

As used herein, "delaying" development of Alzheimer's disease means to defer, hinder, slow, retard, stabilize, and/or postpone development of the disease or its symptoms. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects.

"Development" of Alzheimer's disease means the onset and/or progression of Alzheimer's disease within an individual. Alzheimer's disease development can be detectable using standard clinical techniques. However, development also refers to disease progression that may be initially undetectable. For purposes of this disclosure, progression refers to the biological course of the disease state, in this case, as determined by a standard neurological examination, patient interview, or may be determined by more specialized testing such as the detection or monitoring of biological markers of the disease. A variety of these diagnostic tests include, but not limited to, neuroimaging, detecting alterations of levels of specific proteins in the serum or cerebrospinal fluid (e.g. amyloid peptides and Tau), computerized tomography (CT), and magnetic resonance imaging (MRI). "Development" includes occurrence, recurrence, and onset. As used herein "onset" or "occurrence" of Alzheimer's disease includes initial onset and and/or recurrence.

As used herein, administration "in conjunction" includes simultaneous administration and/or administration at different times. Administration in conjunction also encompasses administration as a co-formulation or administration as separate compositions. As used herein, administration in conjunction is meant to encompass any circumstance wherein an anti-Aβ antibody and another agent are administered to an individual, which can occur simultaneously and/or separately. As further enabled herein, it is understood that an anti-Aβ Fab 2286-like antibody and optionally the other agent can be administered at different dosing frequencies or intervals. For example, an anti-Aβ antibody can be administered weekly, while the other agent can be administered less frequently. It is understood that the anti-Aβ antibody and the other agent can be administered using the same route of administration or different routes of administration.

An "individual" (alternatively referred to as a "subject") is a mammal, including a human. Other mammals include, but are not limited to, farm animals (such as cows), sport animals, companion animals (such as cats, dogs, horses), primates, mice and rats.

The Fab 2286-like antibody may be formulated in a pharmaceutical composition with a pharmaceutically acceptable carrier, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Diluents for aerosol or parenteral administration include phosphate buffered saline or normal (0.9%/w/v) saline. Compositions comprising such carriers are formulated by well known conventional methods (see, for example, *Remington's Pharmaceutical Sciences*, 18th edition, A. Gennaro, ed., Mack Publishing Co., Easton, Pa., 1990; and *Remington, The Science and Practice of Pharmacy* 20th Ed. Mack Publishing, 2000).

The Fab 2286-like antibody may include additional modifications which include functionally equivalent antibodies which do not significantly affect their properties and variants which have enhanced or decreased activity and/or affinity. For example, the amino acid sequence of the heavy or light variable region of the Fab 2286-like antibody may be mutated to obtain an antibody with a desired binding affinity to $A\beta_{1-42}$ of $A\beta_{1-43}$ peptide. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody or which provides a particular functionality.

Substitution variants have at least one amino acid residue in the antibody molecule removed and a different residue inserted in its place. The sites of greatest interest for substitutional mutagenesis include the hypervariable regions, but Fc alterations are also contemplated. Conservative substitutions are shown in Table 3 under the heading of "conservative substitutions".

TABLE 3

Amino Acid substitutions

| Original Residue | Conservative Substitutions | Exemplary Substitutions |
| --- | --- | --- |
| Ala (A) | Val | Val; Leu; Ile |
| Arg (R) | Lys | Lys; Gln; Asn |

TABLE 3-continued

Amino Acid substitutions

| Original Residue | Conservative Substitutions | Exemplary Substitutions |
| --- | --- | --- |
| Asn (N) | Gln | Gln; His; Asp; Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. Naturally occurring residues are divided into groups based on common side-chain properties: (1) Non-polar: Norleucine, Met, Ala, Val, Leu, Ile; (2) Polar without charge: Cys, Ser, Thr, Asn, Gin; (3) Acidic (negatively charged): Asp, Glu; (4) Basic (positively charged): Lys, Arg; (5) Residues that influence chain orientation: Gly, Pro; and (6) Aromatic: Trp, Tyr, Phe, His. As taught herein, the Fab 2286-like antibody comprises a substitution of E to an R in the sequence WIGE in the heavy chain variable region of Fab 2286 (wild type).

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund (1997) *Chem. Immunol.* 65:111-128; Wright and Morrison (1997) *TibTECH* 15:26-32). The oligosaccharide side chains of the immunoglobulins affect the protein's function (Boyd et al. (1996) *Mol. Immunol.* 32:1311-1318; Wittwe and Howard (1990) *Biochem.* 29:4175-4180) and the intramolecular interaction between portions of the glycoprotein, which can affect the conformation and presented three-dimensional surface of the glycoprotein (Jefferis and Lund (1997) supra; Wyss and Wagner (1996) *Current Opin. Biotech.* 7:409-416). Oligosaccharides may also serve to target a given glycoprotein to certain molecules based upon specific recognition structures. Glycosylation of antibodies has also been reported to affect antibody-dependent cellular cytotoxicity (ADCC).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al. (1997) *J. Biol. Chem.* 272:9062-9070).

The methods taught herein use antibodies (including pharmaceutical compositions comprising the antibodies) that specifically bind to an Aβ peptide at the C-terminal end. The antibodies are further characterized by any (one or more) of the following characteristics: (a) suppresses formation of amyloid plaques in a subject; (b) reduces amyloid plaques in a subject; (c) treats, prevents, ameliorates one or more symptoms of Alzheimer's disease; (d) improves cognitive function. The antibodies described herein may exhibit a desirable safety profile, for example, the compositions of Fab 2286-like antibody do not cause significant or unacceptable levels or have a reduced level of any one or more of: bleeding in the brain vasculature (cerebral hemorrhage); meningoencephalitis (including changing magnetic resonance scan); elevated white blood count in cerebral spinal fluid; central nervous system inflammation.

The Fab 2286-like antibodies, polynucleotides encoding amino acid chains of the Fab 2286-like antibody, and pharmaceutical compositions described herein can be used in methods for treating, preventing and inhibiting the development of a disease characterized by aberrant deposition of Aβ peptide in the brain of a subject. The methods comprise administering to the subject an effective amount of the Fab 2286-like antibody that specifically binds to the Aβ peptide or the Aβ peptide deposit or a polynucleotide encoding a chain of the antibody.

Without limiting the present disclosure to any one hypothesis or mode of action, the Fab 2286-like antibody can act directly in the brain to induce microglial-mediated removal of Aβ or via the "peripheral sink" route. According to the latter mode of action, the Fab 2286-like antibody does not need to cross the blood-brain barrier to act, but rather, binds Aβ in the blood and shift the equilibrium of Aβ from the CNS to the plasma, where Aβ can be degraded (DeMattos et al. (2001) *Proc Natl Acad Sci USA* 98:8850-8855).

The Fab 2286-like antibodies, polynucleotides encoding an amino acid chain in the antibody, and pharmaceutical compositions described herein can be used in methods for treating, preventing and inhibiting the development of Alzheimer's disease and other diseases associated with altered Aβ or APP expression, or accumulation or deposit of Aβ peptide (collectively termed "Aβ-associated diseases"), such as Down's syndrome, Parkinson's disease, multi-infarct dementia, mild cognitive impairment, cerebral amyloid angiopathy, glaucoma, vascular disorder caused by deposit of Aβ peptide in blood vessels (such as stroke and HCHWA-D). Such methods comprise administering the Fab 2286-like antibodies or a pharmaceutical composition comprising same to the subject. In prophylactic applications, pharmaceutical compositions or medicaments are administered to a patient susceptible to, or otherwise at risk of, Alzheimer's disease (or other Aβ-associated disease) in an amount sufficient to eliminate or reduce the risk, lessen the severity, or delay the onset of the disease, including biochemical, histological and/or behavioral symptoms of the disease, its complications and intermediate pathological phenotypes presenting during development of the disease. In therapeutic applications, compositions or medicaments are administered to a patient suspected of, or already suffering from such a disease in amount sufficient to cure, or at least partially arrest, the symptoms of the disease (biochemical, histological and/or behavioral), including its complications and intermediate pathological phenotypes in development of the disease.

The present disclosure teaches a method of delaying development of a symptom associated with Alzheimer's disease (or other Aβ-associated disease) in a subject comprising administering an effective dosage of a pharmaceutical composition comprising a Fab 2286-like antibody described herein to the subject. Symptoms associated with Alzheimer disease includes, but not limited to, abnormalities of memory, problem solving, language, calculation, visuospatial perception, judgment, and behavior.

This disclosure enables a method of inhibiting or suppressing the formation of amyloid plaques and/or Aβ accumulation in a subject comprising administering an effective dose of a pharmaceutical composition comprising a Fab 2286-like antibody to the subject. In an embodiment, the amyloid plaques are in the brain of the subject. In an embodiment, the amyloid plaques are in the cerebral vasculature of the subject. In an embodiment, the Aβ accumulation is in the circulatory system of the subject.

The instant disclosure teaches a method of reducing amyloid plaques and/or reducing or slowing Aβ accumulation in a subject comprising administering an effective dose of a pharmaceutical composition comprising an Fab 2286-like antibody to the subject an Fab 2286-like antibody. In an embodiment, the amyloid plaques are in the brain of the subject. In an embodiment, the amyloid plaques are in the cerebral vasculature of the subject. In an embodiment, the Aβ accumulation is in the circulatory system of the subject.

Further taught herein is a method of removing or clearing amyloid plaques and/or Aβ accumulation in a subject comprising administering an effective dose of a pharmaceutical composition comprising an Fab 2286-like antibody to the subject an Fab 2286-like antibody. In an embodiment, the amyloid plaques are in the brain of the subject. In some embodiments, the amyloid plaques are in the cerebral vasculature of the subject. In an embodiment, the Aβ accumulation is in the circulatory system of the subject.

The present disclosure is instructional for a method of reducing Aβ peptide in a tissue (such as brain), inhibiting and/or reducing accumulation of Aβ peptide in a tissue (such as brain), and inhibiting and/or reducing toxic effects of Aβ peptide in a tissue (such as brain) in a subject comprising administering an effective dose of a pharmaceutical composition comprising an Fab 2286-like antibody to the subject an Fab 2286-like antibody. Aβ polypeptide may be in soluble, oligomeric, or deposited form. An oligomeric form of Aβ may be composed of 2 or more (e.g. 2 to 50) Aβ polypeptides, which can be a mixture of inter alia $Aβ_{1-40}$, $Aβ_{1-42}$ and $Aβ_{1-43}$ peptides as well as $Aβ_{3-42}$, $Aβ_{4-42}$, $Aβ_{pyroGlu3-42}$ and $Aβ_{pyroGlu11-42}$ and the like.

The present disclosure teaches a method of improving cognition or reversing cognitive decline associated with diseases associated with amyloid deposit of Aβ in a subject, such as Alzheimer's disease, comprising administering an effective dosage of a pharmaceutical composition comprising an Fab 2286-like antibody to the subject an Fab 2286-like antibody.

Effective dosages and schedules for administering the Fab 2286-like antibody may be determined empirically, and making such determinations is within the skill in the art. Those skilled in the art will understand that the dosage of antibody that must be administered will vary depending on, for example, the mammal that will receive the antibody, the route of administration, the particular type of antibody used and other drugs being administered to the mammal. Guidance in selecting appropriate doses for antibody is found in the literature on therapeutic uses of antibodies, e.g., Handbook of Monoclonal Antibodies, Ferrone et al. eds. Noges Publications, Park Ridge, N.J. (1985) ch. 22:303-357; Smith et al. (1977) *Antibodies in Human Diagnosis and Therapy*, Haber et al. eds., Raven Press, New York:365-389. A typical daily dosage of the antibody used alone might range from about 1 µg/kg to up to 100 mg/kg of body weight or more per day, depending on the factors mentioned above. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight, or more, is administered. Antibodies may be administered at lower doses or less frequent at the beginning of the treatment to avoid potential side effect. Administration may be by any route including intracerebral and intravenous. The latter is useful in promoting a "peripheral sink" effect.

In an embodiment, more than one antibody is present. Such compositions may contain at least one, at least two, at least three, at least four, at least five different antibodies which bind to different epitopes on Aβ or which bind to the same epitope but with different binding avidities.

The Fab 2286-like antibody may also be administered to a mammalian subject in combination with effective amounts of one or more other therapeutic agents. The antibody may be administered sequentially or concurrently with the one or more other therapeutic agents. The amounts of antibody and therapeutic agent depend, for example, on what type of drugs are used, the pathological condition being treated, and the scheduling and routes of administration but would generally be less than if each were used individually.

Following administration of antibody to the mammal, the mammal's physiological condition can be monitored in various ways well known to the skilled practitioner. In an embodiment, the mammal is a human, companion animal, simian animal or laboratory test animal such as a mouse or rat.

The instant disclosure further teaches articles of manufacture and kits containing materials useful for treating pathological conditions described herein, such as Alzheimer's disease or other Aβ-associated diseases (such as Down's syndrome, Parkinson's disease, multi-infarct dementia, mild cognitive impairment, cerebral amyloid angiopathy, glaucoma, vascular disorder caused by deposit of Aβ peptide in blood vessels [such as stroke and HCHWA-D]), or detecting or purifying Aβ or APP. The article of manufacture comprises a container with a label. Suitable containers include, for example, bottles, vials, and test tubes. The containers may be formed from a variety of materials such as glass or plastic. The container holds a composition having an active agent which is effective for treating pathological conditions or for detecting or purifying Aβ or APP. The active agent in the composition is an Fab 2286-like antibody and may further include an anti-Fab 2286-like antibody labeled with a reporter molecule or enzyme. The label on the container indicates that the composition is used for treating pathological conditions such as Alzheimer's disease or detecting or purifying Aβ or APP, and may also indicate directions for either in vivo or in vitro use.

The present disclosure also provides kits comprising the Fab 2286-like antibody and/or polynucleotides encoding amino acid chains of Fab 2286-like antibody. In an embodiment, the kit disclosed herein comprises the container described above. In an embodiment, the kit comprises the container described above and a second container comprising a buffer. It may further include other materials desirable from a commercial and user standpoint, including other buffers, diluents, filters, needles, syringes, and package inserts with instructions for performing any methods described herein (such as methods for treating Alzheimer's disease, and methods for inhibiting or reducing accumulation of Aβ peptide in the brain). In kits to be used for detecting or purifying Aβ or APP, the antibody is typically labeled with a detectable marker, such as, for example, a radioisotope, fluorescent compound, bioluminescent compound, a chemiluminescent compound, metal chelator or enzyme.

In an embodiment, described herein is a composition for use in any of the methods described herein, whether in the context of use as a medicament and/or use for manufacture of a medicament. Hence, taught herein is a use of an antibody which binds to $Aβ_{1-40}$ or C-terminally elongated forms thereof or covalently linked multimers thereof, the antibody comprising a modified Fab 2286 wherein a mature heavy chain comprises a modified amino acid sequence set forth in SEQ ID NO: 1 with the proviso that the amino acid residue at position 50 is not glutamic acid, wherein the numbering of the amino acid sequence WIGE in Fab 2286 (SEQ ID NO:1) represents amino acid residues 47 to 50 or comprising one or other more amino acid substitutions, additions and/or deletions to the amino acid sequence of SEQ ID NO:2 in the manufacture of a medicament for the treatment of pathogenic Aβ disease. In an embodiment, the amino acid is selected from the list consisting of alanine, arginine, asparagine, aspartic acid, cysteine, glutamine, glycine, histidine, isoleucine, leucine, lysine, methionine, phenylalanine, proline, serine, threonine, tryptophan, tyrosine, valine, pyrrolysine and selenocysteine. In an embodiment, the amino acid is a basic amino acid residue such as arginine, lysine or histidine. In an embodiment, the amino acid is alanine. In a particular embodiment, the amino acid is arginine. In an embodiment, the Aβ disease is selected from the list consisting of Alzheimer's disease, Down's syndrome, cognitive impairment or memory loss, Parkinson's disease, multi-infarct dementia, cerebral amyloid angiopathy, glaucoma and a vascular disorder caused by pathogenic Aβ peptide in blood vessels (e.g. stroke and hereditary cerebral hemorrhage with amyloidosis-Dutch type [HCHWA-D]).

Another aspect enabled herein is a method of detecting a toxic form of Aβ in a sample from a subject, said method comprising identifying binding between the Aβ form and Fab 2286-like antibody.

Diagnostic applications include the detection of Alzheimer's disease, Down's syndrome, cognitive impairment or memory loss, Parkinson's disease, multi-infarct dementia, cerebral amyloid angiopathy, glaucoma and a vascular disorder caused by pathogenic Aβ peptide in blood vessels (e.g. stroke and hereditary cerebral hemorrhage with amyloidosis-Dutch type [HCHWA-D]) as well as pre-eclampsia.

In an embodiment, the Fab 2286-like antibody is used to detect Alzheimer's disease, HCHWA-D or pre-eclampsia.

Any immunoassay may be used to capture and/or directly identify a toxic form of Aβ. Immunoassays are binding assays. Certain immunoassays contemplated herein are the various types of enzyme linked immunosorbent assays (ELISAs) and radioimmunoassays (RIA) known in the art. However, it will be readily appreciated that detection is not limited to such techniques, and Western blotting, dot blotting, FACS analyses, and the like may also be used.

In an embodiment, the assay is capable of generating quantitative results.

The Fab 2286-like antibody is either labeled with a reporter molecule or the Fab 2286-like antibody is used to bind to or capture the Aβ and a second antibody (directed to Fab 2286-like antibody or a portion of Aβ) labeled with a reporter molecule is used to detect an Fab 2286-like antibody-Aβ complex.

The Fab 2286-like antibody can be used to screen for or capture toxic forms of Aβ. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to Fab 2286-like antibody. Both types of antibodies may be used in detection assays or the Fab 2286-like antibody may be used with a commercially available anti-immunoglobulin antibody.

Both polyclonal and monoclonal antibodies specific for Fab 2286-like antibody are obtainable by immunization with Fab 2286-like antibodies or antigenic fragments thereof and either type is utilizable for immunoassays. The methods of obtaining both types of sera are well known in the art. Polyclonal sera are less preferred but are relatively easily prepared by injection of a suitable laboratory animal with an effective amount of the Fab 2286-like antibody, or antigenic parts thereof, collecting serum from the animal and isolating specific sera by any of the known immunoabsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates, therefore, a method for detecting a toxic form of Aβ in a biological sample from a subject. The method comprising contacting the biological sample with Fab 2286-like antibody for a time and under conditions sufficient for an antibody-polypeptide complex to form, and then detecting the complex. The Fab 2286-like antibody may be labeled with a reporter molecule and this is detected or a labeled anti-Fab 2286-like antibody or generic labeled anti-immunoglobulin antibody is employed to detect the Fab 2286-like antibody-Aβ complex.

A biological sample includes a blood or cerebral spinal fluid sample. For the detection of pre-eclampsia, the sample is urine.

A "labeled" antibody means an antibody labeled with a reporter molecule. By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to a second antibody, generally by means of glutaraldehyde or periodate. As will be readily recognized, however, a wide variety of different conjugation techniques exist, which are readily available to the skilled artisan.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic colour visually detectable with a light microscope. The fluorescent labeled antibody is allowed to bind to a Fab 2286-like antibody-Aβ complex. After washing off the unbound reagent, the remaining tertiary complex is then exposed to the light of the appropriate wavelength the fluorescence observed indicates the presence of the hapten of interest. Immunofluorescence and EIA techniques are both very well established in the art. However, other reporter molecules, such as radioisotope, chemiluminescent or bioluminescent molecules, may also be employed. In an embodiment, taught herein is a dipstick comprising Fab 2286-like antibody immobilized thereon for use in detecting toxic forms of Aβ in a biological sample. In an embodiment, the sample is urine and the condition diagnosed is pre-eclampsia.

EXAMPLES

Aspects of the present disclosure are now further described by the following non-limiting Examples.

Materials and Methods

Antibody Cloning and Expression and Purification

A chimeric antibody was produced incorporating light and heavy chain variable domains of the anti-Aβ murine monoclonal antibody, Mab 2286, described by Rosenthal et al. (US Patent Application Nos. 2004/046512 and 2007/0160616) conjugated, respectively, to human kappa 1 immunoglobulin (hKappa) light chain and gamma-1 immunoglobulin (hG1) heavy chain constant regions. Amino acid sequences for the Fab region of the light (V$_L$+C$_L$) [SEQ ID NO:3] and heavy (V$_H$+C$_H$) [SEQ ID NO: 1] chains of Fab 2286 are shown in Table 4.

Heavy and light chain constructs were each cloned into the pcDNA 3.1 vector (Invitrogen). Plasmids were transformed into E. coli (DH5-alpha, Invitrogen) for amplification under ampicillin selection and purified with a PureLink (Trade Mark) HiPure Plasmid Megaprep Kit (Invitrogen) according to the manufacturer's instructions. Recombinant expression plasmids were then transfected into FreeStyle (Trade Mark) 293-F cells to allow expression of the recombinant chimeric antibody.

FreeStyle (Trade Mark) 293-F cells were cultured in FreeStyle expression medium (Invitrogen), and maintained at 37° C. with an atmosphere of 8% v/v $CO_2$. Transient transfections were performed using 293Fectin transfection reagent (Invitrogen) according to the manufacturer's instructions. Cultures of 1000 mL were shaken in a Cellbag (Trade Mark) 2 L (flow rate: 0.1-0.15 Lpm) on a bioreactor system. Cultures were supplemented with 0.1% Pluronic F68 (Invitrogen) and 0.5% Lucratone Lupin (Millipore) 4 and 24 hours post transfection, respectively, and the rocking angle adjusted to 9° after 24 hours. Six days post-transfection the cell culture supernatants were harvested by centrifugation at 1000×g.

Harvested conditioned media was filtered through a 0.22 μm filter and applied to a MabSelect SuRe HiTrap Protein A HP Column (5 ml, Hitrap, GE Life Sciences, Sweden) previously equilibrated with PBS. Antibody was eluted with 0.1 M sodium citrate pH 3.5 and collected into 10% v/v final volume of 3.0 M Tris pH 8.0. Antibody was buffer exchanged into PBS using a HiLoad desalting column 26/10 (GE Life Sciences, Sweden) and concentrated to 1 mg/mL with a centrifugal concentrator (Amicon ultra, 50 kDa MWCO) for storage at −80° C.

For expression and purification of Fab2286-like antibody fragment, synthetic DNA cloned into pcDNA3.1 expression vectors were obtained from Genscript for expression of the heavy and light chains. The N-terminal signal peptides were incorporated for the heavy chain (MGWSWIFLFLVSGTG-GVLSE) and light chain (MESQTQVLMS LLFWVS-GTCG). The heavy chain was expressed as a Hexa-histidine tagged construct, with the tag at the C-terminus of the chain. DNA constructs were transformed into DH5α E. coli for amplification under ampicillin selection and purified with a PureLink (Trade Mark) HiPure Plasmid Megaprep Kit (Invitrogen) according to the manufacturer's instructions. Recombinant expression plasmids were then co-transfected into FreeStyle (Trade Mark) 293-F cells (Invitrogen) to allow expression of the recombinant antibody fragment.

293-F cells were cultured in FreeStyle expression medium (Invitrogen), and maintained at 310 K with an atmosphere of 8% v/v $CO_2$. The expression was performed in 4 L batches in a Certomat Ct plus incubator (Sartorius) by doing co-transfection of 1×10$^6$ cells/mL with both DNA and 293Fectin transfection reagent (Invitrogen) according to the manufacturer's instructions. Cultures were supplemented with 5 mL/L of 10% v/v Pluronic F68 (Invitrogen), 5 mg/L Lucratone Lupin (Millipore) 4 hours post transfection, and 5 mg/L of glucose 2 days post-transfection. The cell culture supernatants were harvested by centrifugation at 500×g, and the media collected for purification.

4 L of harvested media was concentrated to 200 mL by tangental flow filtration system (Millipore Proflux M12). The concentrated media was centrifuged at 20000×g for 30 minutes before being purified by immobilised-metal affinity chromatography. The supernatant containing Fab was incubated for 1 hour with equilibrated Ni-NTA affinity resin (Qiagen). The mixture was washed 4 times with 20 mM Tris pH 8.0, 150 mM NaCl and 20 mM imidazole. The protein of interest was eluted with 20 mM Tris pH 8.0, 150 mM NaCl and 500 mM imidazole. Eluted sample was further purified by size exclusion chromatography with a HiLoad Superdex 200 20/60 run in PBS on an AKTApurifier (GE Healthcare). Fractions were concentrated to 2 mg/mL with a centrifugal concentrator (Amicon ultra, 10 kDa MWCO).

Purification of Fab

Fab fragments were prepared using the Immunopure Fab Preparation kit (Pierce Biotechnology). IgG (10 mg) was digested with 0.5 mL of the 50% w/v immobilized papain slurry overnight at room temperature. The immobilized papain was removed by centrifugation (3000×g for 3 minutes) and the supernatant containing the digested sample was loaded onto a 1 mL HiTrap Protein A column (GE Life Sciences, Sweden). Fractions containing the clean Fab fragments were pooled and dialyzed over night in 20 mM HEPES pH 7.0. The dialyzed sample was concentrated with a Centriprep-10 centrifugal concentrator to 4 mg/mL (10 kDa MWCO, Millipore). The digestion and purification steps were monitored by SDS-PAGE.

Amyloid-β Peptides

Peptides corresponding to residues 1-28 (Aβ28), 1-40 (Aβ40) and 1-42 (Aβ42) of the amyloid-β sequence (1-DAEFRHDSGYEVHHQKLVFFAEDVGSNK-GAIIGLMVGGVVIA-42) [SEQ ID NO:6] were obtained from commercial sources: Aβ28 (AnaSpec, San Jose, Calif., USA); Aβ40 and Aβ42 (GenicBio BioTech Co., Shanghai, China). Each of the Aβ peptides was resuspended in 100% (v/v) 2,2,2-trifluoroethanol (TFE) and aliquoted to give 100 μg per Eppendorf tube. All aliquots were freeze-dried for 4 hours and stored at −80° C. until required.

SDS-PAGE and Western Blot

Aβ peptides (100 μg) were dissolved in 2 μL of 10 μM NaOH, then made up to a volume of 100 μL with PBS. Samples of Aβ40 and Aβ42 were prepared in advance and aged at room temperature for either 24 hours or 21 days. A 1:1 molar ratio of Aβ40 and Aβ42 was also prepared and allowed to age overnight before running on SDS-PAGE. Aβ28 was used as a negative control and prepared on the day along with fresh samples of Aβ40 and Aβ42.

An aliquot of 0.5 μg of all aged and freshly prepared Aβ peptides in non-reducing Lamelii loading dye was run on 12% w/v SDS polyacrilamide gel (NuPage; Invitrogen). Gels were run in triplicate, one gel was Coomassie stained with InstantBlue (Expedon) and the other two were transferred for 1 hour at 4° C. to nitrocellulose membrane (Millipore).

Following Western transfer, the nitrocellulose membrane was blocked with 3% w/v BSA in PBS with 0.1% v/v Tween-20 (PBS-T) overnight at 4° C. The membrane was incubated with either Mab 2286 (1:5000) or Mab WO2 (1:2000) in 3% v/v BSA, PBS-T for 1 hour at room temperature. It was then washed four times in PBS-T for 15 minutes each. The blot was then incubated with 1:5000 Protein A-HRP (Millipore) in PBS-T for 1 hour at room temperature. It was washed a further four times in PBS-T for 15 minutes. The membrane was incubated with SuperSignal West Pico chemiluminescent (Pierce) for 5 minutes, exposed for 1 minute to X-ray film (Super RX; Fuji) and developed.

Crystallization

Initial crystallization screening resulted in small needles of crystals that were subsequently optimized by a combination of the Additive Screen (Hampton Research) and grid screening varying pH and PEG concentration. The best crystals were grown in 100 mM citric acid pH 5.5, 20% v/v 2-propanol and 20% w/v PEG 4000. All crystals were grown using by vapor diffusion using 2 μL hanging drops at 22° C. Crystals were soaked in a cryoprotectant (mother liquor plus 15% v/v glycerol) for several minutes prior to mounting in a $N_2$ stream at 100 K.

Structure Determination

Diffraction data from a single crystal of Fab 2286 were collected on the MXI beamline of the Australian Synchrotron (Melbourne, Australia) with an ADSC Quantum 210r detector. Data collection were controlled using Blue-Ice software (McPhillips et al. (2002) *J. Synchroton Radiat* 9:401-406). All diffraction data were acquired from one crystal frozen at 100 K. Data collection statistics are summarized in Table 5.

Accession Numbers

The coordinates for the Fab 2286 structure have been deposited in the Protein Data Bank under the accession number 3U0W.

TABLE 4

Amino acid sequences of the chimeric Fab 2286 light and heavy chains

Light Chain (hKppa)
DIQMTQTTSSLSASLGDRVTISCSASQGISNYLNWFQQKPDGTVKLLIY
YTSSLHSGVPSRFSGSGSGTDYSLTISNLEPEDIATYYCQQYRKLPYTF
GGGTKLEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC (SEQ ID NO: 3)

Heavy Chain (hG1)
EVKLLESGGGLVQPGGSLKISCAASGFDFSRYWMNWVRQAPGKGLEWIG
EINPDSSTINYTPSLKDKFIISRDNAKNTLYLQMSKVRSEDTAIYYCAR
QMGYWGQGTTLTVSSASTKGPSVFPLAPSSKSTSGGTAALGCLVKDYFP
EPVTVSWNSGALTSGVHTFPAVLQSSGLYSLSSVVTVPSSSLGTQTYIC
NVNHKPSNTKVDKKVEPKSC (SEQ ID NO: 10)

Example 1

Western Blot Analysis

Antibody recognition of Aβ peptides is confounded by not only the range of different length peptides produced, but by their propensity to form a range of higher order complexes. In order to explore the specificity of Mab 2286, a number of different Aβ peptide preparations were examined. These included denatured and freshly dissolved Aβ28, Aβ40 and Aβ42, which would be mostly monomeric in solution. The peptides were allowed to oligomerize/aggregate both in isolation and as a mixture of the two most common peptides, Aβ40 and Aβ42, for 24 hours to 21 days. These were then analyzed by SDS-PAGE and detected by Coomassie stain (FIG. 1A), Western Blot with chimeric anti-Aβ Mab 2286 as the primary antibody (FIG. 1B) and Western Blot with murine anti-Aβ Mab WO2 as the primary antibody (FIG. 1C).

Mab WO2 was used as the reference antibody as the 3-D Aβ recognition epitope was previously determined, which involves the free side chains of $A\beta_{2-7}$ (Miles et al. (2008) *J Mol Biol* 377:181-192). Consistent with the epitope recognition of Mab WO2, specific bands corresponding to Aβ28, Aβ40 and Aβ42 were detected as well as a range of higher molecular weight Aβ species observed for all of the aged peptides (FIG. 1C), indicating that the aging protocol used was sufficient to generate a number of oligomeric forms.

By contrast, quite strikingly, Mab 2286 was highly selective and sensitive in detecting monomeric Aβ40, with no cross-reactivity with any of the other aggregated forms apart from a minor Aβ40 dimeric species (FIG. 1B, Lane 2). There was no cross-reactivity with either the Aβ28 or Aβ42 sample (FIG. 1B, Lane 6 and 4 respectively). Interestingly, no monomeric Aβ40 was detected in the sample that had been left to age for 21 days (FIG. 1B Lane 1), suggesting that all monomeric Aβ40 had reacted to form oligomers/aggregates. The preparation comprised a mixture of Aβ40 and Aβ42 and was allowed to age overnight. Under these conditions the level of monomeric Aβ40 detected by Mab 2286 was significantly reduced (FIG. 1B Lane 5) relative to freshly prepared Aβ40 alone (the starting concentration of monomeric Aβ40 is the same as the sample in Lane 2) indicating that it has formed higher molecular weight oligomers in the presence of Aβ42.

Rosenthal and co-workers showed that Mab 2286 is specific for Aβ terminating at residue 40. They also showed that single point alanine mutations across the terminal residues (35-MVGGVV-40 [SEQ ID NO:8]) modulated binding affinity (Rosenthal et al. US Patent Application No. 2007/0160616). Unlike the N-terminal region of Aβ, the C-terminal region is hydrophobic. When combined, these data indicate that Mab 2286 recognises the hydrophobic side chains of Aβ40 at the C-terminus that are predominantly available in the monomeric state or available for recruitment from perhaps dimers or higher order complexes.

Example 2

Structure of Fab 2286

High resolution (2 Å) structure of a chimeric form of an antigen binding fragment of Mab 2286 [Fab 2286], was determined (Table 5). The structure of Fab 2286 reveals that it is a typical immunoglobulin Fab heavy/light chain heterodimer with an elbow angle of 185.2°. The putative Aβ binding groove in the Fab2286 crystal structure was calculated to be approximately 1900 $Å^3$ using Fred Receptor (v2.2.5, OpenEye Scientific Software, Inc., http://www.eyesopen.com).

TABLE 5

Data collection and refinement statistics

| Crystal | Fab 2286 |
|---|---|
| Data collection | |
| Space group | $P2_12_12_1$ |
| Unit-cell parameters | |
| a (Å) | 64.0 |
| b (Å) | 81.3 |
| c (Å) | 108.5 |
| Maximum resolution (Å) | 2.0 |
| Total observations | 437605 |
| Unique reflections used | 39062 |
| Redundancy | 11.7 (5.0)[a] |
| Completeness (%) | 95.7 (71.7) |
| I/σ$_I$ | 27.9 (2.3) |
| $R_{SYM}$ (%)[b] | 9.7 (83.1) |
| Final refinement statistics | |
| Resolution (Å) | 2.0 |
| Total no. of atoms | 3511 |
| No. of waters | 304 |
| R-factor (%)[c] | 18.9 |
| R-free (%)[d] | 23.5 |
| r.m.s.d. bond lengths (Å) | 0.021 |
| r.m.s.d. bond angles (°) | 2.0 |

TABLE 5-continued

Data collection and refinement statistics

| Mean B-factor | |
|---|---|
| Protein m.c. (s.c.) | 28.4 (33.1) |
| Solvent | 41.2 |
| Ramachandran regions (%) | |
| Favored | 90.0 |
| Allowed | 9.7 |
| Disallowed | 0.3 |

[a]The values in parentheses are for the highest resolution bin.
[b]$R_{SYM} = \Sigma_{hkl}\Sigma_i |I_i - <I>|/|<I>|$, where $I_i$ is the intensity for the ith measurement of an equivalent reflection with indices h, k, l.
[c]R-factor = $\Sigma ||F_{obs}| - |F_{calc}||/\Sigma|F_{obs}|$, where $F_{obs}$ and $F_{calc}$ are the observed and calculated structure factor amplitudes respectively.
[d]R-free was calculated with 5% of the diffraction data that were selected randomly and not used throughout refinement.

Example 3

Generation of Fab 2286-Like Antibody

Mab 2286 exhibits specificity for the carboxyl terminus of $A\beta_{40}$ and shows no significant cross reactivity with C-terminally extended peptides such as $A\beta_{42}$ and $A\beta_{43}$. Antibody binding to $A\beta_{40}$ is not inhibited by $A\beta_{38}$ in competitive binding assays, and binding is similarly modulated by conservative alanine single point mutations across the mapped residues (35-MVGGVV-40 [SEQ ID NO:8]).

The structure of chimeric Fab 2286 determined herein reveals a mechanism explaining specificity for the $A\beta_{40}$ C-terminus and involves extensive contacts with the $A\beta_{40}$ Val39 side chain buried in a hydrophobic pocket at the antibody interface. With the side chain of $A\beta_{40}$ Val39 anchored in this way, the side chain of Val40 makes further hydrophobic contacts such that the free carboxyl moiety can hydrogen bond with Asn35(H). C-terminally extended $A\beta$ peptides would lose this potential hydrogen bond and the additional residues would force the ligand backbone to adopt a conformation that is incompatible with the $A\beta$ binding site.

The Western Blot analysis shown in FIG. 1 indicates that, unlike the N-terminus, this hydrophobic C-terminal epitope is buried in oligomeric/aggregated synthetic $A\beta_{40}$, as only bands correlating with monomer and dimer molecular weights are detected by the binding fragment of Mab 2286, i.e. Fab 2286. It is concluded that the epitope of $A\beta$ recognized by Fab 2286 is buried in higher order oligomeric assemblies is consistent with the crystal structures of the peptide reported by Colletier et al. (2011) *Proc Natl Acad Sci USA* 108(41):16938-43. In that work, fibril-like structures of the peptide were shown to exhibit parallel and anti-parallel β-sheet stacked forms. The two steric zippers reported identify "knobs-in-holes" type packing, with Val39 (and Ile41) constituting the buried 'knobs' accommodated by the "holes" enabled by the presence of the glycine residues.

It is known that amyloid plaques in the Alzheimer's diseased brain are mainly composed of C-terminally extended species such as $A\beta_{42}$ and $A\beta_{43}$, and these represent significant pathogens in Alzheimer's disease. According to the "peripheral sink" hypothesis (DeMattos et al. (2001) supra), anti-$A\beta$ antibodies need not cross the blood brain barrier to act, but rather, bind $A\beta$ in the blood and shift the equilibrium of $A\beta$ from the CNS to the plasma, where $A\beta$ can be degraded.

A His-tagged fusion of Fab 2286 chains was generated using human kappa-1 immunoglobulin (hkappa-1) light chain and gamma-1 immunoglobulin (hG1) heavy chain constant regions. In the Fab 2286, Glu50 is mutated to Arg (Glu50Arg) on the heavy chain. The Fab 2286-like antibody produced recognized the hydrophobic C-terminal epitope available in monomeric forms of $A\beta$, but one which can also accommodate C-terminally extended $A\beta$ peptides which have a greater propensity to aggregate or nucleate/accelerate oligomerization.

Figure 2:
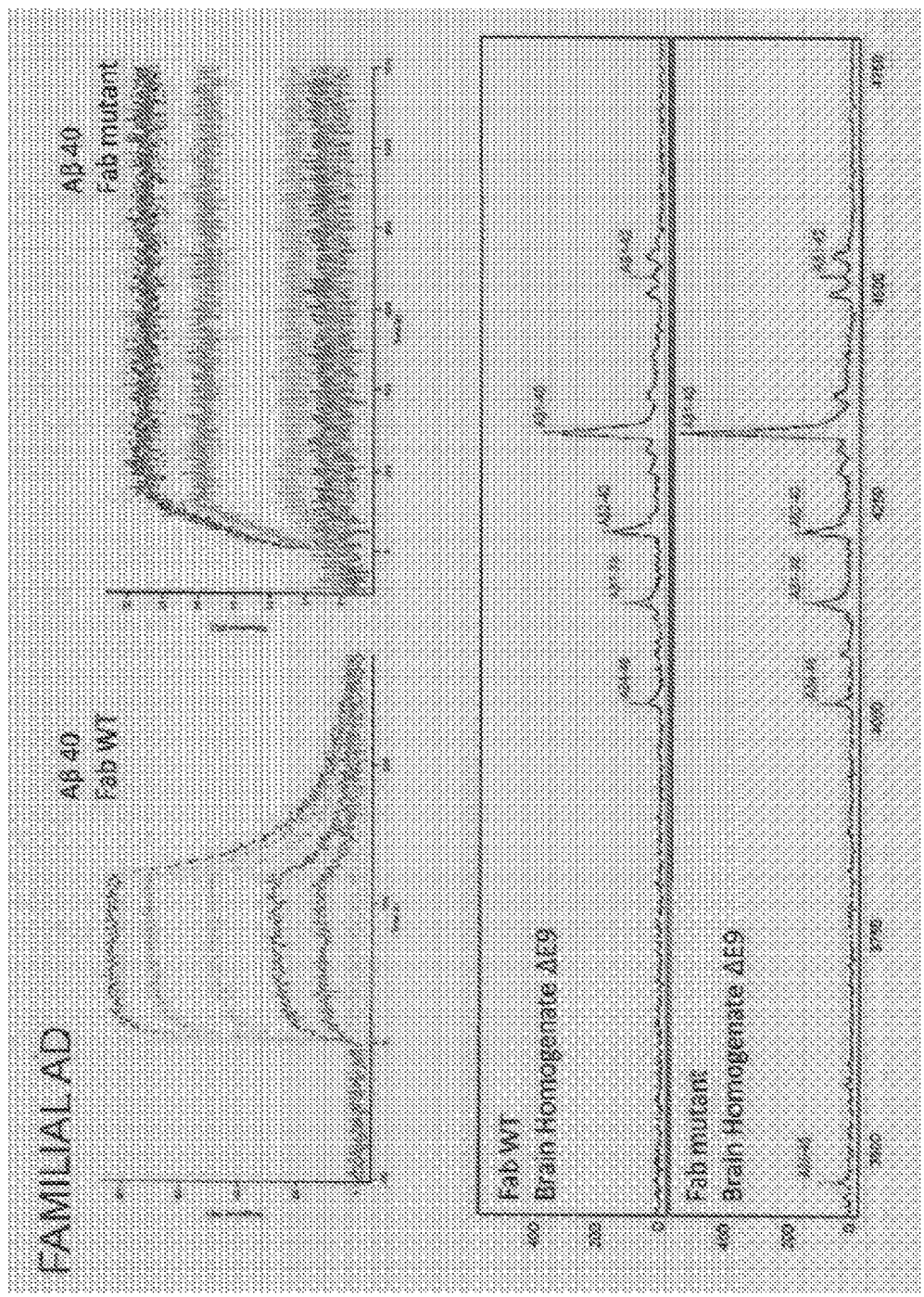
FIG. 2 is a graphical representation of the binding characteristics of Fab 2286 (Aβ Fab wt) and the Fab 2286-like antibody (Aβ Fab mutant) in tissue from a familial Alzheimer's diseased brain and against synthetic peptide Aβ$_{1-42}$.
Figure 3:
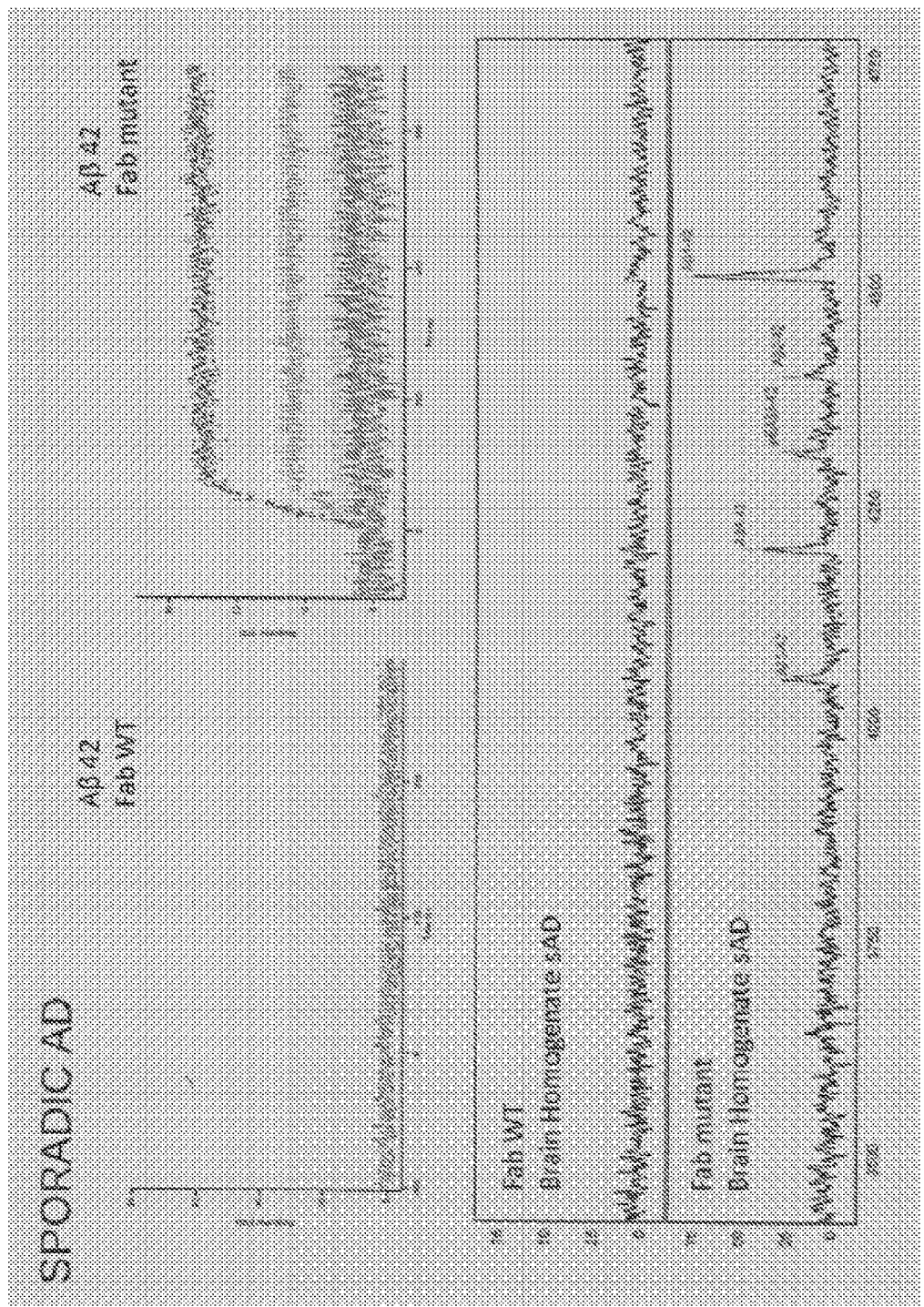
FIG. 3 is a graphical representation of the binding characteristics of Fab 2286 (Aβ Fab wt) and the Fab 2286-like antibody (Aβ Fab mutant) in tissue from a sporadic Alzheimer's diseased brain and against synthetic peptide Aβ$_{1-42}$.

Synthetic DNA constructs corresponding to heavy and light chains of Fab 2286 were ordered from Genscript and subcloned into the pcDNA 3.1 vector (Invitrogen) for expression in mammalian cells. A single point mutation was introduced into the heavy chain protein sequence based on a computational analysis of Fab 2286, an antibody fragment that has only low micromolar affinity for amyloid beta peptide terminating at residue 40. The mutant Fab was designed to recognize $A\beta_{1-40}$. It also was able to bind toxic C-terminally extended peptides including $A\beta_{1-42}$ and $A\beta_{1-43}$. The resultant mutant Fab not only bound the longer length peptides but also did so with low nanomolar affinity. FIGS. 2 and 3 compare the $A\beta$ binding profiles between Fab 2286 and the Fab 2286-like antibody Glu50Arg Fab mutant against synthetic $A\beta$ species and against $A\beta$ species in brain tissue affected by familial and sporadic Alzheimer's disease respectively.

Example 4

Generation of Fab 2286-Like Antibody on a Murine Scaffold

A murinized form of the Fab 2286-like antibody was generated. To murinized the antibody, the following sequences were employed:

```
Monoclonal antibody 2286 (Mab 2286) nucleic acid
sequence: heavy chain [variable domain and
constant domain 1 (CH1)]; [SEQ ID NO: 12]:
gaggtgaagcttctcgagtctggaggtggcctggtgcagcctggaggatc cctgaaactctcctgtgcagcctcaggattcgattttagtagatactgga tgaattgggtccggcaggctccagsgaaagggctagaatggattggagaa attaatccagatagcagtacgataaactatacgccatctctaaaggataa attcatcatctccagagacaacgccaaaaatacgctgtacctgcaaatga gcaaagtgagatctgaggacacagcccttattactgtgcaagacaaatg ggctactggggccaaggcaccactctcacagtctcctcagccaaaacgac accccatctgtctatccactggccctggatctgctgcccaaactaact ccatggtgaccctgggatgcctggtcaagggctatttccctgagccagtg acagtgacctggaactctggatccctgtccagcggtgtgcacaccttccc agctgtcctgcagtctgacctctacactctgagcagctcagtgactgtcc cctccagcacctggcccagcgagaccatcacctgcaacgttgcccacccg gccagcagcaccaaggtggacaagaaaattgtgcccagggattgt and the light chain: (SEQ ID NO: 14):
gatatccagatgacacagactacatcctccctgtctgcctctctgggaga cagagtcaccatcagttgcagtgcaagtcagggcattagcaattatttaa actggtttcagcagaaaccagatggaactgnaaactcctgatctattaca catcaagtttacactcaggagtcccatcaaggttcagtggcagtgggtct
```

```
gggacagattattctctcaccatcagcaacctggaacctgaagatattgc cacttactattgtcagcagtataggaagcttccgtacacgttcggaggg gggaccaagctggaaataaaacgggctgatgctgcaccaactgtatccat cttcccaccatccagtgagcagttaacatctggaggtgcctcagtcgtgt gcttcttgaacaacttctaccccaaagacatcaatgtcaagtggaagatt gatggcagtgaacgacaaaatggcgtcctgaacagttggactgatcagga cagcaaagacagcacctacagcatgagcagcaccctcacgttgaccaagg acgagtatgaacgacataacagctatacctgtgaggccactcacaagaca tcaacttcacccattgtcaagagcttcaacaggaatgagtgt
```

The Mab 2286 amino acid sequence: heavy chain
[variable domain and constant domain 1 (CH)];
[SEQ ID NO: 13]:
EVKLLESGGGLVQPGGSLKLSCAASGFDFSRYWMNWVRQAPGKGLEWIGE

INPDSSTINYTPSLKDKFIISRDNAKNTLYLQMSKVRSEDTALYYCARQM

GYWGQGTTLTVSSAKTTPPSVYPLAPGSAAQTNSMVTLGCLVKGYFPEPV

TVTWNSGSLSSGVHTFPAVLQSDLYTLSSSVTVPSSTWPSETVTCNVAHP

ASSTKVDKKIVPRDC and the light chain; (SEQ ID NO: 15):
DIQMTQTTSSLSASLGDRVTISCSASQGISNYLNWFQQKPDGTVKLLIYY

TSSLHSGVPSRFSGSGSGTDYSLTISNLEPEDIATYYCQQYRKLPYTFGG

GTKLEIKRADAAPTVSIFPPSSEQLTSGGASVVCFLNNFYPDKINVKWKI

DGSERQNGVLNSWTDQDSKDSTYSMSSTLTLTKDEYERHNSYTCEATHKT

STSPIVKSFNRNEC

The Fc portion from a murine gamma heavy chain (GenBank: AAA75163.1) was added to the heavy chain Fab portion sequence. The synthetic DNA construct was:

Gene name: MurineHeavyA_OPT, Length: 1391 bp,
Sequence (SEQ ID NO: 16):
GAGGTCAAACTGCTGGAGAGTGGAGGGGGACTGGTGCAGCCAGGCGGGT

CACTGAAGCTGAGCTGCGCCGCTTCCGGCTTCGACTTTTCCCGGTACTG

GATGAATTGGGTGAGACAGGCTCCCGGAAAAGGCCTGGAGTGGATCGGG

GAAATTAATCCTGATAGCTCCACCATCAACTACACACCAAGTCTGAAGG

ACAAATTCATCATTTCACGCGATAACGCAAAGAATACTCTGTATCTGCA

GATGTCTAAAGTGCGAAGTGAGGACACCGCACTGTACTATTGTGCAAGA

CAGATGGGATACTGGGGACAGGGAACCACACTGACCGTGTCTAGTGCTA

AGACTACCCCTCCCAGCGTGTATCCTCTGGCACCTGGCTCCGCAGCACAG

ACCAATTCTATGGTGACACTGGGCTGTCTGGTCAAGGGGTACTTCCCTG

AGCCAGTCACAGTGACTTGGAACAGCGGCAGCCTGTCAAGCGGCGTGCA

CACCTTTCCTGCCGTCCTGCAGAGCGATCTGTATACACTGTCCTCTAGT

GTCACTGTGCCCTCAAGCACCTGGCCTTCCGAGACCGTGACATGCAACG

TCGCCCATCCTGCTTCCTCTACAAAGGTGGACAAGAAAATCGTCCCACG

AGATTGCGCTGTAAACCATGCATTTGTACTGTCCCCGAAGTGAGTTCAG

TCTTCATCTTTCCACCCAAGCCAAAAGACGTGCTGACTATTACCCTGAC

ACCCAAGGTCACATGCGTGGTCGTGGATATCAGCAAAGACGATCCCGAG

GTGCAGTTCTCCTGGTTTGTCGACGATGTCGAAGTGCACACAGCCCAGA

CTCAGCCCAGGGAGGAACAGTTCAATTCTACCTTTCGCTCTGTGAGTGA

GCTGCCTATTATGCATCAGGACTGGCTGAATGGAAAGGAATTCAAATGC

AGAGTGAACTCTGCTGCATTTCCCGCTCCTATCGAGAAGACTATTAGCA

AGACCAAAGGCAGGCCTAAAGCCCCACAGGTGTACAATCCCTCCACC

CAAGGAACAGATGGCTAAGGATAAAGTGAGCCTGACATGTATGATCACT

GACTTCTTTCCCGAGGATATTACCGTGGAATGGCAGTGGAACGGGCAGC

CCGCAGAGAACTATAAGAATACACAGCCTATTATGGACACTGATGGATC

ATACTTCGTGTATAGCAAGCTGAACGTCCAGAAATCTAATTGGGAAGCC

GGCAACACTTTTAGCCTGTAGTGTGCTGCATGAAGGACTGCATAACCAT

CATACTGAAAAGTCACTGTCTCATTCACCAGGCAAA and the amino acid sequence (SEQ ID NO: 17):
EVKLLESGGGLVQPGGSLKLSCAASGFDFSRYWMNWVRQAPGKGLEWIG

EINPDSSTINYTPSLKDKFIISRDNAKNTLYLQMSKVRSEDTALYYCAR

QMGYWQGTTLTVSSAKTTPPSVYPLAPGSAAQTNSMVTLGCLVKGYFPE

PVTVTWNSGSLSSGVHTFPAVLQSDLYTLSSSVTVPSSTWPSETVTCNV

AHPASSTKVDKKIVPRDCGCKPCICTVPEVSSVFIFPPKPKDVLTITLT

PKVTCVVVDISKDDPEVQFSWFVDDVEVHTAQTQPREEQFNSTFRSVSE

LPIMHQDWLNGKEFKCRVNSAAFPAPIEKTISKTKGRPKAPQVYTIPPP

KEQMAKDKVSLTCMITDFFPEDITVWQWNGQPAENYKNTQPIMDTDGSY

FVYSKLNVQKSNWEAGNTFTCSVLHEGLHNHHTEKSLSHSPGK

The mutant Fab 2286-like antibody (with the Glu to Arg substitution) was derived from mutagenesis of that sequence yielding:

Variant name, Murine Heavy B, Variant sequence
(SEQ ID NO: 18):
GAGGTCAAACTGCTGGAGAGTGGAGGGGGACTGGTGCAGCCAGGCGGGTC

ACTGAAGCTGAGCTGCGCCGCTTCCGGCTTCGACTTTTCCCGGATACTGG

ATGAATTGGGTGAGACAGGCTCCCGGAAAAGGCCTGGAGTGGATCGGGCG

TATTAATCCTGATAGCTCCACCATCAACTACACACCAAGTCTGAAGGACA

AATTCATCATTTCACGCGATAACGCAAAGAATACTCTGTGATCTGCAGAT

GTCTAAAGTGCGAAGTGAGGACACCGCACTGTACTATTGTGCAAGACAGA

TGGGATACTGGGGACAGGGAACCACACTGACCGTGTCTAGTGCTAAGACT

ACCCCTCCCAGCGTGTATCCTCTGGCACCTGGCTCCGCAGCACAGACCAA

TTCTATGGTGACACTGGGCTGTCTGGTCAAGGGGTACTTCCCTGAGCCAG

TCACAGTGACTTGGAACAGCGGCAGCCTGTCAAGCGGCGTGCACACCTTT

CCTGCCGTCCTGCAGAGCGATCTGTATACACTGTCCTCTAGTGTCACTGT

GHCCCTCAAGCACCTGGCCTTCCGAGACCGTGACATGCAACGTCGCCCAT

CCTGCTTCCTCTACAAAGGTGGACAAGAAAATCGTCCCACGAGATTGCGG

CTGTAAACCATGCATTTGTACTGTCCCCGAAGTGAGTTCAGTCTTCATCT

TTCCACCCAAGCCAAAAGACGTGCTGACTATTACCCTGACACCCAAGGTC

-continued

```
ACATGCGTGGTCGTGGATATCAGCAAAGACGATCCCGAGGTGCAGTTCTC

CTGGTTTGTCGACGATGTCGAAGTGCACACAGCCCAGACTCAGCCCAGGG

AGGAACAGTTCAATTCTACCTTTCGCTCGTGAGTGAGCTGCCTATTATGC

ATCAGGACTGGCTGAATGGAAAGGAATTCAAATGCAGAGTGAACTCTGCT

GCATTTCCCGCTCCTATCGAGAAGACTATTAGCAAGACCAAAGGCAGGCC

TAAAGCCCCACAGGTGTACACAATCCCTCCACCCAAGGAACAGATGGCTA

AGGATAAAGTGAGCCTGACATGTATGATCACTGACTTCTTTCCCGAGGAT

ATTACCGTGGAATGGCAGTGGAACGGGCAGCCCGCAGAGAACTATAAGAA

TACACAGCCTATTATGGACACTGATGGATCATACTTCGTGTATAGCAAGC

TGAACGTCCAGAAATCTAATTGGGAAGCCGGCAACACTTTTACCTGTAGT

GTGCTGCATGAAGGACTGCATAACCATCATACTGAAAAGTCACTGTCTCA

TTCACCAGGCAAA
``` and the amino acid sequence (SEQ ID NO: 19)
```
EVKLLESGGGLVQPGGSLKLSCAASGFDFSRYWMNWVRQAPGKGLEWIG

EINPDSSTINYTPSLKDKFIISRDNAKNTLYLQMSKVRSEDTALYYCAR

QMGYWQGTTLTVSSAKTTPPSVYPLAPGSAAQTNSMVTLGCLVKGYFPE

PVTVTWNSGSLSSGVHTFPAVLQSDLYTLSSSVTVPSSTWPSETVTCNV

AHPASSTKVDKKIVPRDCGCKPCICTVPEVSSVFIFPPKPKDVLTITLT

PKVTCVVVDISKDDPEVQFSWFVDDVEVHTAQTQPREEQFNSTFRSVSE

LPIMHQDWLNGKEFKCRVNSAAFPAPIEKTISKTKGRPKAPQVYTIPPP

KEQMAKDKVSLTCMITDFFPEDITVWQWNGQPAENYKNTQPIMDTDGSY

FVYSKLNVQKSNWEAGNTFTCSVLHEGLHNHHTEKSLSHSPGK
```

The synthetic DNA light chain construct is:

Murine Light_OPT, Length: 725 bp, Sequence
(SEQ ID NO: 20):
```
GATATTCAGATGACTCAGACTACTTCTTCCCTGTCTGCAAGTCTGGGGGA

CCGAGTGACAATCTCATGCAGCGCCTCCCAGGGAATTTCCAACTACCTGA

ATTGGTTCCAGCAGAAGCCTGATGGCACAGTGAAACTGCTGATCTACTAT

ACTAGCTCCCTGCACAGTGGGGTCCCATCAAGATTTTCTGGAAGTGGCTC

AGGGACCGACTATAGCCTGACAATCTCCAACCTGGAGCCAGAAGATATTG

CCACTTACTATTGCCAGCAGTACCGGAAGCTGCCCTATACTTTCGGCGGG

GGAACCAAGCTGGAGATCAAAAGAGCTGACGCCGCTCCCACCGTGAGCAT

TTTTCCCCCTTCTAGTGAACAGCTGACCTCTGGCGGGCAAGTGTGGTCT

GTTTCCTGAACAACTTCTACCCTAAAGACATCAACGTGAAGTGGAAAATT

GATGGAAGCGAGAGGCAGAACGGCGTCCTGAATTCCTGGACCGACCAGGA

TAGCAAGGACTCCACATATTCTATGTCAAGCACCCTGACACTGACTAAAG

ATGAGTACGAACGCCATAATAGCTATACATGTGAAGCTACTCATAAGACC

TCTACCTCTCCTATTGTGAAATCTTTTAACGAAATGAATGT
```
and the amino acid sequence (SEQ ID NO: 21):
```
DIQMTQTTSSLSASLGDRVTISCSASQGISNYLNWFQQKPDGTVKLLIYY

TSSLHSGVPSRFSGSGSGTDYSLTISNLEPEDIATYYCQQYRKLPYTFGG

GTKLEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKT

STSPIVKSFNFNEC
```

The murinized Fab 2286-like antibody is used in animal model studies.

Example 5

Animal Model

Mouse model protocols for the evaluation of Fab 2286-like antibody are established. Efficacy of the antibody is tested in Tg2576 mice which over express $A\beta_{40}$ or other mice which over express elongated forms of $A\beta$. To test Fab 2286-lie antibody or a derivative thereof, APP/PS1 mice are used. An anti-$A\beta$ drug efficacy protocol such as by Kenche el al. (2013) *Angewandte Chemie International Edition* 52):3374-3378 is a reliable template to formulate a study design. These mice generate significant quantities of both $A\beta_{40}$ and $A\beta_{42}$ in the brain and are amyloid positive at around 7-8 months, cognitively impaired at 9-10 months. Mice are purchased at ~3 months of age from The Jackson Laboratory, Bar Harbor, Me., USA, and are allowed 2 months for acclimatization at a housing facility. APP/PS1 mice are randomly assigned to different treatment groups, (e.g. 10 mg/kg Fab 2286-like antibody, 10 mg/kg vehicle control). Behavioral assessment and tissue analysis follow protocols established by Kenche et al. (2013) supra. Treatment begins at 5 months before amyloid deposition has begun in three arms of 15 animals each (based on a Power statistical analysis for a significant outcome). Behavioral assessments begin at 7 months of age by Y-maze and water platform techniques as described by Kenche et al. (2013) supra. Weekly dosing is administered by oral gavage until 10 months of age when tissue is collected and subject to immunohistochemical analysis and examined for differential $A\beta_{40}/A\beta_{42}$ profiles by SELDI-TOF MS and other IP/MS methods.

Example 6

Detection of Pre-Eclampsia

Urine samples are obtained from healthy women, healthy pregnant women and pregnant women diagnosed with pre-eclampsia. The levels and species of $A\beta$ are determined in each group. In an alternative, cerebral spinal fluid is tested. However, a urine sample is far less invasive. Fab 2286-like antibody is used to either capture the $A\beta$ species which is then detected using a labeled anti-immunoglobulin antibody or the Fab 2286-like antibody is labeled itself. It is expected that pregnant women with pre-eclampsia will exhibit elevated levels of brain-derived toxic $A\beta$ species comprising C-terminally elongated forms.

The Fab 2286-like antibody may also be used in the development of a dipstick or other similar approach to detect toxic $A\beta$ in urine of pregnant women.

Example 7

Generation of Modified Fab 2286 Heavy Chains

Using the techniques disclosed herein or known to the skilled artisan, a range of substitutions is made at amino acid residue 50 in the heavy chain variable region of Fab 2286.

The amino acid sequence set forth in SEQ ID NO:2 comprises an arginine in place of a glutamic acid at residue 50. This creates the amino acid sequence comprising WIGR.

Other substitutions are selected from WIGA, WIGR, WIGN, WIGD, WIGC, WIGQ, WJGG, WIGH, WIGI, WIGL, WIGK, WIGM, WIGF, WIGP, WIGS, WIGT, WIGW, WIGY, WIGV, WIGO and WIGU.

An antibody comprising any of these substitutions from glutamic acid are readily tested as disclosed herein for the ability to bind to $A\beta_{1-40}$ or C-terminally elongated forms.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Adolfsson et al. (2012) *J. Neuroscience* 32(28):9677-9689
Altschul et al. (1997) *Nucl. Acids. Res.* 25:3389
Ausubel et al. (In: *Current Protocols in Molecular Biology*, John Wiley & Sons Inc. 1994-1998
Bacskai et al. (2002) *J. Neurosci.* 22:7873-7878
Bard et al. (2000) *Nature Medicine* 6:916-919
Bard et al. (2003) *Proc. Natl. Acad. Sci. USA* 100:2023-2028
Bonner and Laskey (1974) *Eur. J. Biochem.* 46:83
Boyd et al. (1996) *Mol. Immunol.* 32:1311-1318
Colletier et al. (2011) *Proc Natl Acad Sci USA* 108(41): 16938-43
Das el al. (2003) *J. Neurosci.* 23:8532-9538
DeMattos et al. (2001) *Proc Natl Acad Sci USA* 98:8850-8855
Hardy (1996) *Ann Med* 28:255-258
Hardy (2014) *N Engl. Med* 370(4):377-378
Handbook of Monoclonal Antibodies, Ferrone et al. eds. Noges Publications, Park Ridge, N.J. (1985) ch. 22:303-357
Hse et al. (1997) *J. Biol. Chem.* 272:9062-9070
Jefferis and Lund (1997) *Chem. Immunol.* 65:111-128
Kenche et al. (2013) *Angewandte Chemie International Edition* 52:3374-3378
Liu et al. (2014) *Mol Neurobiol*:PMID 24733588
Marmur and Doty (1962) *J. Mol. Biol.* 5:109
McPhillips et al. (2002) *J. Synchroton Radiat* 9:401-406
Miles et al. (2008) *J Mol Biol* 377:181-192
Miles et al. (2013) *Sci Rep* 3:1-8
Panza et al. (2014) *Expert Opin Biol Ther:* 1-12 PMID 24981190
*Remington's Pharmaceutical Sciences,* 18th edition, A. Gennaro, ed., Mack Publishing Co., Easton, Pa., 1990; and *Remington, The Science and Practice of Pharmacy* 20th Ed. Mack Publishing, 2000
Rosenthal et al. (2004) US Patent Application No. 2004/046512
Rosenthal et al. (2007) US Patent Application No. 2007/016616
Rosenthal et al. U.S. Pat. No. 7,807,165
Salloway et al. (2009) *Neurology* 73:2061-2070
Schenk et al. (1999) *Nature* 400:173-177
Selkoe (2001) *Physiol Rev* 81:741-766
Smith et al. (1977) *Antibodies in Human Diagnosis and Therapy*, Haber et al. eds., Raven Press, New York:365-389
Tanzi et al. (1996) *Neurobiol Dis* 3:159-168
Wallace et al. (1996) *Protein Eng* 8:127-134
Wittwe and Howard (1990) *Biochem.* 29:4175-4180
Wright and Morrison (1997) *TibTECH* 15:26-32
Wyss and Wagner (1996) *Current Opin. Biotech.* 7:409-416

We claim:

1. An isolated antibody or antigen binding fragment thereof which binds to $A\beta_{1-40}$ and a C-terminally elongated form thereof, said antibody or antigen binding fragment thereof comprising a mature heavy chain variable region comprising the amino acid sequence as set forth in residues 1 to 111 of SEQ ID NO: 11.

2. The isolated antibody or antigen binding fragment thereof of claim 1 wherein the C-terminally elongated form of $A\beta_{1-40}$ is selected from $A\beta_{1-42}$, $A\beta_{1-43}$, $A\beta_{3-42}$, $A\beta_{4-42}$, $A\beta_{pyroGlu3-42}$ and $A\beta_{pyroGlu11-42}$.

3. The isolated antibody or antigen binding fragment thereof of claim 1 conjugated to constant regions of light and heavy chains.

4. The isolated antibody or antigen binding fragment thereof of claim 3 comprising the amino acid sequence of residues 1 to 216 of SEQ ID NO:11.

5. An isolated nucleic acid molecule comprising a nucleotide sequence encoding the amino acid sequence as set forth in residues 1-111 of SEQ ID NO: 1.

6. A method of treating a pathogenic $A\beta$ disease comprising administering an isolated antibody or antigen binding fragment thereof of claim 1.

7. The method of claim 6 wherein the $A\beta$ disease is associated with or characterized by pathogenic forms of $A\beta$ selected from $A\beta_{1-42}$, $A\beta_{1-43}$, $A\beta_{3-42}$, $A\beta_{4-42}$, $A\beta_{pyroGlu3-42}$ and $A\beta_{pyroGlu11-42}$ in tissue or fluid.

8. The method of claim 7 wherein the tissue is brain tissue.

9. The method of claim 7 wherein the fluid is circulatory blood fluid.

10. The method of claim 6 wherein the disease is selected from Alzheimer's disease, Down's syndrome, cognitive impairment or memory loss, Parkinson's disease, multi-infarct dementia, cerebral amyloid angiopathy, glaucoma, and a vascular disorder caused by pathogenic $A\beta$ peptide in blood vessels.

11. The method of claim 10 wherein the vascular disorder is stroke or hereditary cerebral hemorrhage with amyloidosis-Dutch type (HCHWA-D).

12. The method of claim 10 wherein the disease is Alzheimer's disease.

13. A method of detecting a toxic form of $A\beta$ in a sample from a subject, said method comprising identifying binding between the $A\beta$ form and the antibody or antigen binding fragment thereof of claim 1.

14. The method of claim 13 wherein the antibody or antigen binding fragment thereof is labeled with a reporter molecule.

15. The method of claim 13 wherein the antibody or antigen binding fragment thereof is identified by a labeled anti-immunoglobulin antibody.

16. The method of claim 13 for the detection of a disease selected from the list consisting of Alzheimer's disease, Down's syndrome, cognitive impairment or memory loss, Parkinson's disease, multi-infarct dementia, cerebral amyloid angiopathy, glaucoma, pre-eclampsia and a vascular disorder caused by pathogenic $A\beta$ peptide in blood vessels.

* * * * *

SEQUENCE LISTING

```
<160> NUMBER OF SEQ ID NOS: 21

<210> SEQ ID NO 1
<211> LENGTH: 215
<212> TYPE: PRT
<213> ORGANISM: artificial
<220> FEATURE:
<223> OTHER INFORMATION: Amino acid sequence of heavy chain of Fab 2286
      antibody

<400> SEQUENCE: 1

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gln Met Gly Tyr Trp Gly Gln Gly Thr Thr Leu Thr Val Ser
            100                 105                 110
```

```
Ser Ala Lys Thr Thr Pro Pro Ser Val Tyr Pro Leu Ala Pro Gly Ser
        115                 120                 125

Ala Ala Gln Thr Asn Ser Met Val Thr Leu Gly Cys Leu Val Lys Gly
    130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys
    210                 215

<210> SEQ ID NO 2
<211> LENGTH: 215
<212> TYPE: PRT
<213> ORGANISM: artificial
<220> FEATURE:
<223> OTHER INFORMATION: Amino acid sequence of heavy chain of Fab
      2286-like antibody

<400> SEQUENCE: 2

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Arg Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gln Met Gly Tyr Trp Gly Gln Gly Thr Thr Leu Thr Val Ser
            100                 105                 110

Ser Ala Lys Thr Thr Pro Pro Ser Val Tyr Pro Leu Ala Pro Gly Ser
        115                 120                 125

Ala Ala Gln Thr Asn Ser Met Val Thr Leu Gly Cys Leu Val Lys Gly
    130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys
    210                 215

<210> SEQ ID NO 3
<211> LENGTH: 214
<212> TYPE: PRT
```

```
<213> ORGANISM: artificial
<220> FEATURE:
<223> OTHER INFORMATION: Amino acid sequence of light chain (hkappa)

<400> SEQUENCE: 3

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Arg Lys Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 28
<212> TYPE: PRT
<213> ORGANISM: artificial
<220> FEATURE:
<223> OTHER INFORMATION: Amino acid sequence of Abeta1-28

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

<210> SEQ ID NO 5
<211> LENGTH: 40
<212> TYPE: PRT
<213> ORGANISM: artificial
<220> FEATURE:
<223> OTHER INFORMATION: Amino acid sequence of Abeta1-40

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30
```

```
Gly Leu Met Val Gly Gly Val Val
        35                  40

<210> SEQ ID NO 6
<211> LENGTH: 42
<212> TYPE: PRT
<213> ORGANISM: artificial
<220> FEATURE:
<223> OTHER INFORMATION: Amino acid sequence of Abeta1-42

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 7
<211> LENGTH: 43
<212> TYPE: PRT
<213> ORGANISM: artificial
<220> FEATURE:
<223> OTHER INFORMATION: Amino acid sequence of Abeta1-43

<400> SEQUENCE: 7

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40

<210> SEQ ID NO 8
<211> LENGTH: 6
<212> TYPE: PRT
<213> ORGANISM: artificial
<220> FEATURE:
<223> OTHER INFORMATION: Amino acid sequence of Abeta35-40

<400> SEQUENCE: 8

Met Val Gly Gly Val Val
1               5

<210> SEQ ID NO 9
<211> LENGTH: 437
<212> TYPE: PRT
<213> ORGANISM: artificial
<220> FEATURE:
<223> OTHER INFORMATION: Amino acid sequence of murinized Fab 2286-like
      antibody heavy chain conjugated to human gamma-1 immunoglobulin
      (hG1) hevy constant region with Glu50Arg substitution

<400> SEQUENCE: 9

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Arg Ile Asn Pro Asp Ser Ser Thr Ile Asn Tyr Thr Pro Ser Leu
    50                  55                  60
```

```
Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
             85                  90                  95

Ala Arg Gln Met Gly Tyr Trp Gly Gln Gly Thr Thr Leu Thr Val Ser
            100                 105                 110

Ser Ala Lys Thr Thr Pro Pro Ser Val Tyr Pro Leu Ala Pro Gly Ser
        115                 120                 125

Ala Ala Gln Thr Asn Ser Met Val Thr Leu Gly Cys Leu Val Lys Gly
    130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys Gly Cys Lys Pro Cys Ile Cys Thr Val
    210                 215                 220

Pro Glu Val Ser Ser Val Phe Ile Phe Pro Pro Lys Pro Lys Asp Val
225                 230                 235                 240

Leu Thr Ile Thr Leu Thr Pro Lys Val Thr Cys Val Val Val Asp Ile
                245                 250                 255

Ser Lys Asp Asp Pro Glu Val Gln Phe Ser Trp Phe Val Asp Asp Val
            260                 265                 270

Glu Val His Thr Ala Gln Thr Gln Pro Arg Glu Glu Gln Phe Asn Ser
        275                 280                 285

Thr Phe Arg Ser Val Ser Glu Leu Pro Ile Met His Gln Asp Trp Leu
    290                 295                 300

Asn Gly Lys Glu Phe Lys Cys Arg Val Asn Ser Ala Ala Phe Pro Ala
305                 310                 315                 320

Pro Ile Glu Lys Thr Ile Ser Lys Thr Lys Gly Arg Pro Lys Ala Pro
                325                 330                 335

Gln Val Tyr Thr Ile Pro Pro Lys Glu Gln Met Ala Lys Asp Lys
            340                 345                 350

Val Ser Leu Thr Cys Met Ile Thr Asp Phe Phe Pro Glu Asp Ile Thr
        355                 360                 365

Val Glu Trp Gln Trp Asn Gly Gln Pro Ala Glu Asn Tyr Lys Asn Thr
    370                 375                 380

Gln Pro Ile Met Asp Thr Asp Gly Ser Tyr Phe Val Tyr Ser Lys Leu
385                 390                 395                 400

Asn Val Gln Lys Ser Asn Trp Glu Ala Gly Asn Thr Phe Thr Cys Ser
                405                 410                 415

Val Leu His Glu Gly Leu His Asn His Thr Glu Lys Ser Leu Ser
            420                 425                 430

His Ser Pro Gly Lys
            435

<210> SEQ ID NO 10
<211> LENGTH: 216
<212> TYPE: PRT
<213> ORGANISM: artificial
<220> FEATURE:
<223> OTHER INFORMATION: Amino acid sequence of chimeric Fab2286
``` antibody heavy chain variable region

<400> SEQUENCE: 10

Glu Val Lys Leu Leu Glu Ser Gly Gly Gly Leu Val Gln Pro Gly Gly
1               5                   10                  15

Ser Leu Lys Ile Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Ile Tyr Tyr Cys
                85                  90                  95

Ala Arg Gln Met Gly Tyr Trp Gly Gln Gly Thr Thr Leu Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215

<210> SEQ ID NO 11
<211> LENGTH: 222
<212> TYPE: PRT
<213> ORGANISM: artificial
<220> FEATURE:
<223> OTHER INFORMATION: Amino acid seuqnece of chimeric Fab 2286-like
      antibody heavy chain variable region

<400> SEQUENCE: 11

Glu Val Lys Leu Leu Glu Ser Gly Gly Gly Leu Val Gln Pro Gly Gly
1               5                   10                  15

Ser Leu Lys Ile Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Arg Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Ile Tyr Tyr Cys
                85                  90                  95

Ala Arg Gln Met Gly Tyr Trp Gly Gln Gly Thr Thr Leu Thr Val Ser
            100                 105                 110

Ser Ala Ser Thr Lys Gly Pro Ser Val Phe Pro Leu Ala Pro Ser Ser

|           | 115       |           | 120       |           | 125       |           |
|-----------|-----------|-----------|-----------|-----------|-----------|-----------|

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys His His His His His His
    210                 215                 220

```
<210> SEQ ID NO 12
<211> LENGTH: 645
<212> TYPE: DNA
<213> ORGANISM: artificial
<220> FEATURE:
<223> OTHER INFORMATION: Monoclonal antibody 2286 nucleic acid seuqence:
      heavy chain

<400> SEQUENCE: 12
gaggtgaagc ttctcgagtc tggaggtggc ctggtgcagc ctggaggatc cctgaaactc      60
tcctgtgcag cctcaggatt cgattttagt agatactgga tgaattgggt ccggcaggct     120
ccagggaaag gctagaatg gattggagaa attaatccag atagcagtac gataaactat      180
acgccatctc taaggataa attcatcatc tccagagaca acgccaaaaa tacgctgtac      240
ctgcaaatga gcaaagtgag atctgaggac acagcccttt attactgtgc aagacaaatg     300
ggctactggg gccaaggcac cactctcaca gtctcctcag ccaaaacgac ccccccatct     360
gtctatccac tggcccctgg atctgctgcc caaactaact ccatggtgac cctgggatgc     420
ctggtcaagg gctatttccc tgagccagtg acagtgacct ggaactctgg atccctgtcc     480
agcggtgtgc acaccttccc agctgtcctg cagtctgacc tctacactct gagcagctca     540
gtgactgtcc cctccagcac ctggcccagc gagaccgtca cctgcaacgt tgcccacccg     600
gccagcagca ccaaggtgga caagaaaatt gtgcccaggg attgt                     645

<210> SEQ ID NO 13
<211> LENGTH: 215
<212> TYPE: PRT
<213> ORGANISM: artificial
<220> FEATURE:
<223> OTHER INFORMATION: Mab2286 amino acid sequence: heavy chain

<400> SEQUENCE: 13
```

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys

```
                    85                  90                  95
Ala Arg Gln Met Gly Tyr Trp Gly Gln Gly Thr Thr Leu Thr Val Ser
                100                 105                 110

Ser Ala Lys Thr Thr Pro Pro Ser Val Tyr Pro Leu Ala Pro Gly Ser
            115                 120                 125

Ala Ala Gln Thr Asn Ser Met Val Thr Leu Gly Cys Leu Val Lys Gly
        130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys
    210                 215

<210> SEQ ID NO 14
<211> LENGTH: 642
<212> TYPE: DNA
<213> ORGANISM: artificial
<220> FEATURE:
<223> OTHER INFORMATION: Monoclonal antibody 2286 nucleic acid seuqence:
      light chain

<400> SEQUENCE: 14
gatatccaga tgacacagac tacatcctcc ctgtctgcct ctctgggaga cagagtcacc      60
atcagttgca gtgcaagtca gggcattagc aattatttaa actggtttca gcagaaacca     120
gatggaactg ttaaactcct gatctattac acatcaagtt tacactcagg agtcccatca     180
aggttcagtg gcagtgggtc tgggacagat tattctctca ccatcagcaa cctggaacct     240
gaagatattg ccacttacta ttgtcagcag tataggaagc ttccgtacac gttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gt                        642

<210> SEQ ID NO 15
<211> LENGTH: 214
<212> TYPE: PRT
<213> ORGANISM: artificial
<220> FEATURE:
<223> OTHER INFORMATION: Mab 2886 amino acid sequence: light chain

<400> SEQUENCE: 15

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Phe Gln Gln Lys Pro Asp Gly Thr Val Lys Leu Leu Ile
            35                  40                  45

Tyr Tyr Thr Ser Ser Leu His Ser Gly Val Pro Ser Arg Phe Ser Gly
```

```
            50                  55                  60
Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Arg Lys Leu Pro Tyr
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 16
<211> LENGTH: 1311
<212> TYPE: DNA
<213> ORGANISM: artificial
<220> FEATURE:
<223> OTHER INFORMATION: Murine heavy A_Opt, Length: 1391 bp

<400> SEQUENCE: 16

```
gaggtcaaac tgctggagag tggaggggga ctggtgcagc caggcgggtc actgaagctg      60
agctgcgccg cttccggctt cgacttttcc cggtactgga tgaattgggt gagacaggct     120
cccggaaaag gcctggagtg gatcggggaa attaatcctg atagctccac catcaactac     180
acaccaagtc tgaaggacaa attcatcatt tcacgcgata cgcaaagaa tactctgtat      240
ctgcagatgt ctaaagtgcg aagtgaggac accgcactgt actattgtgc aagacagatg     300
ggatactggg gacagggaac cacactgacc gtgtctagtg ctaagactac ccctcccagc     360
gtgtatcctc tggcacctgg ctccgcagca cagaccaatt ctatggtgac actgggctgt     420
ctggtcaagg gtacttccc tgagccagtc acagtgactt ggaacagcgg cagcctgtca      480
agcggcgtgc acacctttcc tgccgtcctg cagagcgatc tgtatacact gtcctctagt     540
gtcactgtgc cctcaagcac ctggccttcc gagaccgtga catgcaacgt cgcccatcct     600
gcttcctcta caaaggtgga caagaaaatc gtcccacgag attgcggctg taaaccatgc     660
atttgtactg tccccgaagt gagttcagtc ttcatctttc cacccaagcc aaaagacgtg     720
ctgactatta ccctgacacc caaggtcaca tgcgtggtcg tggatatcag caaagacgat     780
cccgaggtgc agttctcctg gtttgtcgac gatgtcgaag tgcacacagc ccagactcag     840
cccaggagg aacagttcaa ttctaccttt cgctctgtga gtgagctgcc tattatgcat      900
caggactggc tgaatggaaa ggaattcaaa tgcagagtga actctgctgc atttcccgct     960
cctatcgaga agactattag caagaccaaa ggcaggccta agccccaca ggtgtacaca     1020
atccctccac caaggaaca gatggctaag gataaagtga gcctgacatg tatgatcact     1080
gacttctttc ccgaggatat taccgtggaa tggcagtgga acgggcagcc cgcagagaac     1140
```

-continued

```
tataagaata cacagcctat tatggacact gatggatcat acttcgtgta tagcaagctg      1200
aacgtccaga atctaattg ggaagccggc aacactttta cctgtagtgt gctgcatgaa       1260
ggactgcata accatcatac tgaaaagtca ctgtctcatt caccaggcaa a              1311
```

```
<210> SEQ ID NO 17
<211> LENGTH: 437
<212> TYPE: PRT
<213> ORGANISM: artificial
<220> FEATURE:
<223> OTHER INFORMATION: Murine heavy A_Opt amino acid sequence

<400> SEQUENCE: 17
```

| | | | | | | | | | | | | | | |
|---|---|---|---|---|---|---|---|---|---|---|---|---|---|---|
| Glu | Val | Lys | Leu | Leu | Glu | Ser | Gly | Gly | Gly | Leu | Val | Gln | Pro | Gly | Gly |
| 1 | | | | 5 | | | | | 10 | | | | | 15 | |

Ser Leu Lys Leu Ser Cys Ala Ala Ser Gly Phe Asp Phe Ser Arg Tyr
           20                  25                  30

Trp Met Asn Trp Val Arg Gln Ala Pro Gly Lys Gly Leu Glu Trp Ile
         35                  40                  45

Gly Glu Ile Asn Pro Asp Ser Ser Thr Ile Asn Tyr Thr Pro Ser Leu
     50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
             85                  90                  95

Ala Arg Gln Met Gly Tyr Trp Gly Gln Gly Thr Thr Leu Thr Val Ser
            100                 105                 110

Ser Ala Lys Thr Thr Pro Pro Ser Val Tyr Pro Leu Ala Pro Gly Ser
        115                 120                 125

Ala Ala Gln Thr Asn Ser Met Val Thr Leu Gly Cys Leu Val Lys Gly
    130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys Gly Cys Lys Pro Cys Ile Cys Thr Val
    210                 215                 220

Pro Glu Val Ser Ser Val Phe Ile Phe Pro Pro Lys Pro Lys Asp Val
225                 230                 235                 240

Leu Thr Ile Thr Leu Thr Pro Lys Val Thr Cys Val Val Val Asp Ile
                245                 250                 255

Ser Lys Asp Asp Pro Glu Val Gln Phe Ser Trp Phe Val Asp Asp Val
            260                 265                 270

Glu Val His Thr Ala Gln Thr Gln Pro Arg Glu Glu Gln Phe Asn Ser
        275                 280                 285

Thr Phe Arg Ser Val Ser Glu Leu Pro Ile Met His Gln Asp Trp Leu
    290                 295                 300

Asn Gly Lys Glu Phe Lys Cys Arg Val Asn Ser Ala Ala Phe Pro Ala
305                 310                 315                 320

Pro Ile Glu Lys Thr Ile Ser Lys Thr Lys Gly Arg Pro Lys Ala Pro
                325                 330                 335

```
Gln Val Tyr Thr Ile Pro Pro Lys Glu Gln Met Ala Lys Asp Lys
                340                 345                 350

Val Ser Leu Thr Cys Met Ile Thr Asp Phe Phe Pro Glu Asp Ile Thr
            355                 360                 365

Val Glu Trp Gln Trp Asn Gly Gln Pro Ala Glu Asn Tyr Lys Asn Thr
        370                 375                 380

Gln Pro Ile Met Asp Thr Asp Gly Ser Tyr Phe Val Tyr Ser Lys Leu
385                 390                 395                 400

Asn Val Gln Lys Ser Asn Trp Glu Ala Gly Asn Thr Phe Thr Cys Ser
                405                 410                 415

Val Leu His Glu Gly Leu His Asn His His Thr Glu Lys Ser Leu Ser
            420                 425                 430

His Ser Pro Gly Lys
            435

<210> SEQ ID NO 18
<211> LENGTH: 1311
<212> TYPE: DNA
<213> ORGANISM: artificial
<220> FEATURE:
<223> OTHER INFORMATION: Murine heavy B, variant sequence

<400> SEQUENCE: 18
gaggtcaaac tgctggagag tggaggggga ctggtgcagc caggcgggtc actgaagctg      60
agctgcgccg cttccggctt cgactttttcc cggtactgga tgaattgggt gagacaggct    120
cccggaaaag gcctggagtg gatcgggcgt attaatcctg atagctccac catcaactac    180
acaccaagtc tgaaggacaa attcatcatt tcacgcgata cgcaaagaa tactctgtat      240 ctgcagatgt ctaaagtgcg aagtgaggac accgcactgt actattgtgc aagacagatg    300
ggatactggg gacagggaac cacactgacc gtgtctagtg ctaagactac ccctcccagc    360
gtgtatcctc tggcacctgg ctccgcagca cagaccaatt ctatggtgac actgggctgt    420
ctggtcaagg ggtacttccc tgagccagtc acagtgactt ggaacagcgg cagcctgtca    480
agcggcgtgc acaccttttcc tgccgtcctg cagagcgatc tgtatacact gtcctctagt    540
gtcactgtgc cctcaagcac ctggccttcc gagaccgtga catgcaacgt cgcccatcct    600
gcttcctcta caaaggtgga caagaaaatc gtcccacgag attgcggctg taaaccatgc    660
atttgtactg tccccgaagt gagttcagtc ttcatctttc cacccaagcc aaaagacgtg    720
ctgactatta ccctgacacc caaggtcaca tgcgtggtcg tggatatcag caaagacgat    780
cccgaggtgc agttctcctg gtttgtcgac gatgtcgaag tgcacacagc ccagactcag    840
cccagggagg aacagttcaa ttctaccttt cgctctgtga gtgagctgcc tattatgcat    900
caggactggc tgaatggaaa ggaattcaaa tgcagagtga actctgctgc atttcccgct    960
cctatcgaga agactattag caagaccaaa ggcaggccta agccccacag ggtgtacaca   1020
atccctccac ccaaggaaca gatggctaag gataaagtga gcctgacatg tatgatcact   1080
gacttctttc ccgaggatat taccgtggaa tggcagtgga acgggcagcc cgcagagaac   1140
tataagaata cacagcctat tatggacact gatggatcat acttcgtgta tagcaagctg   1200
aacgtccaga atctaattg ggaagccggc aacacttttta cctgtagtgt gctgcatgaa   1260
ggactgcata accatcatac tgaaaagtca ctgtctcatt caccaggcaa a            1311

<210> SEQ ID NO 19
<211> LENGTH: 437
```

```
<212> TYPE: PRT
<213> ORGANISM: artificial
<220> FEATURE:
<223> OTHER INFORMATION: Murine heavy B amino acid sequence

<400> SEQUENCE: 19
```

| | | | | | | | | | | | | | | |
|---|---|---|---|---|---|---|---|---|---|---|---|---|---|---|
| Glu | Val | Lys | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Lys | Leu | Ser | Cys | Ala | Ala | Ser | Gly | Phe | Asp | Phe | Ser | Arg | Tyr |
| | | | 20 | | | | | 25 | | | | | 30 | | |
| Trp | Met | Asn | Trp | Val | Arg | Gln | Ala | Pro | Gly | Lys | Gly | Leu | Glu | Trp | Ile |
| | | 35 | | | | | 40 | | | | | 45 | | | |
| Gly | Arg | Ile | Asn | Pro | Asp | Ser | Ser | Thr | Ile | Asn | Tyr | Thr | Pro | Ser | Leu |
| | 50 | | | | | 55 | | | | | 60 | | | | |
| Lys | Asp | Lys | Phe | Ile | Ile | Ser | Arg | Asp | Asn | Ala | Lys | Asn | Thr | Leu | Tyr |
| 65 | | | | | 70 | | | | | 75 | | | | | 80 |
| Leu | Gln | Met | Ser | Lys | Val | Arg | Ser | Glu | Asp | Thr | Ala | Leu | Tyr | Tyr | Cys |
| | | | | 85 | | | | | 90 | | | | | 95 | |
| Ala | Arg | Gln | Met | Gly | Tyr | Trp | Gly | Gln | Gly | Thr | Thr | Leu | Thr | Val | Ser |
| | | | 100 | | | | | 105 | | | | | 110 | | |
| Ser | Ala | Lys | Thr | Thr | Pro | Pro | Ser | Val | Tyr | Pro | Leu | Ala | Pro | Gly | Ser |
| | | 115 | | | | | 120 | | | | | 125 | | | |
| Ala | Ala | Gln | Thr | Asn | Ser | Met | Val | Thr | Leu | Gly | Cys | Leu | Val | Lys | Gly |
| | 130 | | | | | 135 | | | | | 140 | | | | |
| Tyr | Phe | Pro | Glu | Pro | Val | Thr | Val | Thr | Trp | Asn | Ser | Gly | Ser | Leu | Ser |
| 145 | | | | | 150 | | | | | 155 | | | | | 160 |
| Ser | Gly | Val | His | Thr | Phe | Pro | Ala | Val | Leu | Gln | Ser | Asp | Leu | Tyr | Thr |
| | | | | 165 | | | | | 170 | | | | | 175 | |
| Leu | Ser | Ser | Ser | Val | Thr | Val | Pro | Ser | Ser | Thr | Trp | Pro | Ser | Glu | Thr |
| | | | | 180 | | | | | 185 | | | | | 190 | |
| Val | Thr | Cys | Asn | Val | Ala | His | Pro | Ala | Ser | Ser | Thr | Lys | Val | Asp | Lys |
| | | | 195 | | | | | 200 | | | | | 205 | | |
| Lys | Ile | Val | Pro | Arg | Asp | Cys | Gly | Cys | Lys | Pro | Cys | Ile | Cys | Thr | Val |
| | | 210 | | | | | 215 | | | | | 220 | | | |
| Pro | Glu | Val | Ser | Ser | Val | Phe | Ile | Phe | Pro | Pro | Lys | Pro | Lys | Asp | Val |
| 225 | | | | | 230 | | | | | 235 | | | | | 240 |
| Leu | Thr | Ile | Thr | Leu | Thr | Pro | Lys | Val | Thr | Cys | Val | Val | Val | Asp | Ile |
| | | | | 245 | | | | | 250 | | | | | 255 | |
| Ser | Lys | Asp | Asp | Pro | Glu | Val | Gln | Phe | Ser | Trp | Phe | Val | Asp | Asp | Val |
| | | | 260 | | | | | 265 | | | | | 270 | | |
| Glu | Val | His | Thr | Ala | Gln | Thr | Gln | Pro | Arg | Glu | Glu | Gln | Phe | Asn | Ser |
| | | | 275 | | | | | 280 | | | | | 285 | | |
| Thr | Phe | Arg | Ser | Val | Ser | Glu | Leu | Pro | Ile | Met | His | Gln | Asp | Trp | Leu |
| | | 290 | | | | | 295 | | | | | 300 | | | |
| Asn | Gly | Lys | Glu | Phe | Lys | Cys | Arg | Val | Asn | Ser | Ala | Ala | Phe | Pro | Ala |
| 305 | | | | | 310 | | | | | 315 | | | | | 320 |
| Pro | Ile | Glu | Lys | Thr | Ile | Ser | Lys | Thr | Lys | Gly | Arg | Pro | Lys | Ala | Pro |
| | | | | 325 | | | | | 330 | | | | | 335 | |
| Gln | Val | Tyr | Thr | Ile | Pro | Pro | Lys | Glu | Gln | Met | Ala | Lys | Asp | Lys | |
| | | | 340 | | | | | 345 | | | | | 350 | | |
| Val | Ser | Leu | Thr | Cys | Met | Ile | Thr | Asp | Phe | Phe | Pro | Glu | Asp | Ile | Thr |
| | | | 355 | | | | | 360 | | | | | 365 | | |
| Val | Glu | Trp | Gln | Trp | Asn | Gly | Gln | Pro | Ala | Glu | Asn | Tyr | Lys | Asn | Thr |
| | | 370 | | | | | 375 | | | | | 380 | | | |

```
Gln Pro Ile Met Asp Thr Asp Gly Ser Tyr Phe Val Tyr Ser Lys Leu
385                 390                 395                 400

Asn Val Gln Lys Ser Asn Trp Glu Ala Gly Asn Thr Phe Thr Cys Ser
                405                 410                 415

Val Leu His Glu Gly Leu His Asn His His Thr Glu Lys Ser Leu Ser
            420                 425                 430

His Ser Pro Gly Lys
        435

<210> SEQ ID NO 20
<211> LENGTH: 642
<212> TYPE: DNA
<213> ORGANISM: artificial
<220> FEATURE:
<223> OTHER INFORMATION: Murine light_Opt length: 725bp

<400> SEQUENCE: 20
gatattcaga tgactcagac tacttcttcc ctgtctgcaa gtctggggga ccgagtgaca      60
atctcatgca gcgcctccca gggaatttcc aactacctga attggttcca gcagaagcct    120
gatggcacag tgaaactgct gatctactat actagctccc tgcacagtgg ggtcccatca    180
agattttctg gaagtggctc agggaccgac tatagcctga caatctccaa cctggagcca    240
gaagatattg ccacttacta ttgccagcag taccggaagc tgccctatac tttcggcggg    300
ggaaccaagc tggagatcaa aagagctgac gccgctccca ccgtgagcat tttccccct    360 tctagtgaac agctgacctc tggcggggca agtgtggtct gtttcctgaa caacttctac    420
cctaaagaca tcaacgtgaa gtggaaaatt gatggaagcg agaggcagaa cggcgtcctg    480
aattcctgga ccgaccagga tagcaaggac tccacatatt ctatgtcaag caccctgaca    540
ctgactaaag atgagtacga acgccataat agctatacat gtgaagctac tcataagacc    600
tctacctctc ctattgtgaa atcttttaac cgaaatgaat gt                       642

<210> SEQ ID NO 21
<211> LENGTH: 214
<212> TYPE: PRT
<213> ORGANISM: artificial
<220> FEATURE:
<223> OTHER INFORMATION: Murine light_Opt amino acid sequence

<400> SEQUENCE: 21

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Arg Lys Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
```

```
                   130                 135                 140
Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
                210
```